United States Patent
Kameta et al.

(10) Patent No.: US 9,018,156 B2
(45) Date of Patent: Apr. 28, 2015

(54) ORGANIC NANOTUBE HAVING HYDROPHOBIZED INNER SURFACE, AND ENCAPSULATED MEDICINAL AGENT PREPARED USING THE NANOTUBE

(75) Inventors: Naohiro Kameta, Ibaraki (JP); Wuxiao Ding, Ibaraki (JP); Mitsutoshi Masuda, Ibaraki (JP); Hiroyuki Minamikawa, Ibaraki (JP); Momoyo Wada, Ibaraki (JP); Toshimi Shimizu, Ibaraki (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 14/116,182

(22) PCT Filed: Mar. 30, 2012

(86) PCT No.: PCT/JP2012/058724
§ 371 (c)(1),
(2), (4) Date: Jan. 30, 2014

(87) PCT Pub. No.: WO2012/153576
PCT Pub. Date: Nov. 15, 2012

(65) Prior Publication Data
US 2014/0147476 A1    May 29, 2014

(30) Foreign Application Priority Data

May 9, 2011 (JP) .................. 2011-104251
May 9, 2011 (JP) .................. 2011-104438

(51) Int. Cl.
| | |
|---|---|
| *A61K 9/00* | (2006.01) |
| *B82Y 40/00* | (2011.01) |
| *A61K 47/48* | (2006.01) |
| *C07K 1/113* | (2006.01) |
| *B82Y 5/00* | (2011.01) |
| *B82Y 30/00* | (2011.01) |

(52) U.S. Cl.
CPC .................. *A61K 9/0092* (2013.01); *B82Y 5/00* (2013.01); *B82Y 40/00* (2013.01); *A61K 47/48961* (2013.01); *C07K 1/1136* (2013.01); *A61K 47/48869* (2013.01); *B82Y 30/00* (2013.01)

(58) Field of Classification Search
CPC .................. A61K 47/48869; A61K 47/48961; A61K 9/0092; B82Y 5/00; B82Y 30/00; B82Y 40/00; C07K 1/1136
See application file for complete search history.

(56) References Cited

FOREIGN PATENT DOCUMENTS

| | | |
|---|---|---|
| JP | 2002-322190 | 11/2002 |
| JP | 4174702 | 8/2008 |
| JP | 2008-264897 | 11/2008 |
| JP | 2009-136975 | 6/2009 |
| JP | 2010-5706 | 1/2010 |
| JP | 2012 051828 | * 8/2010 ............... C07H 5/06 |
| JP | 2011-184391 | 9/2011 |
| JP | 2012-51828 | 3/2012 |
| WO | 2006/090821 | 8/2006 |

OTHER PUBLICATIONS

Singh et al., 2009, Organic functionalisation and characterization of single-walled carbon nanotubes, The Royal Society of Chemistry, 38: 2214-2230.*

(Continued)

*Primary Examiner* — Amber D Steele
(74) *Attorney, Agent, or Firm* — Wenderoth, Lind & Ponack, L.L.P.

(57) ABSTRACT

Provided is an organic nanotube having a hydrophobized inner surface, formed by molecules including an asymmetric bipolar lipid molecule represented by the following General Formula (1) and a derivative thereof represented by the following General Formula (2), wherein the organic nanotube has a hydrophilized outer surface and a hydrophobized inner surface of a hollow cylinder and is formed by binary self-assembly, the organic nanotube encapsulates a hydrophobic guest in the hollow cylinder, has a function of refolding a denatured protein, and has a function of sustainably-releasing a hydrophobic drug according to the change in hydrophobicity of the inner surface of the tube or external stimulus,

[Chemical Formula 1]

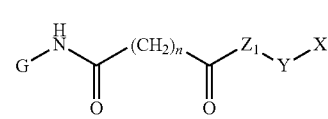

General Formula (1)

[Chemical Formula 2]

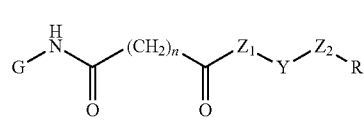

General Formula (2)

In Formulas (1) and (2), wherein the same symbols have the same meanings, G is a 1-glucopyranosyl group or 2-glucopyranosyl group, and n is an integer of 12 to 22. Particularly, an asymmetric bipolar lipid molecule and an ester thereof respectively represented by general formulae (1) and (2) wherein n is an integer of 18 to 22, both of $Z_1$ and $Z_2$ are single bonds, Y is Gly, m(s) is the same or different integer of 3 to 6, X is OH, and R is a methoxy group, an ethoxy group, or a benzyloxy group are novel substances, and can form a carboxylic acid based asymmetric nanotube by single component self-assembly or binary self-assembly.

20 Claims, 20 Drawing Sheets

(56) References Cited

OTHER PUBLICATIONS

Ju et al., 2011, Electrochemical Biosensing Based on Carbon Nanotubes, Chapter 7, Nanosensing: Principles, Development and Application, pp. 207-239.*

International Search Report issued May 15, 2012 in International (PCT) Application No. PCT/JP2012/058724.

Chen et al., "Preparation of Fluorescent Silica Nanotubes and Their Application in Gene Delivery", Advanced Materials, vol. 17, No. 4, Feb. 23, 2005, pp. 404-407.

Abidian et al., "Conducting-Polymer Nanotubes for Controlled Drug Release", Advanced Materials, vol. 18, 2006, pp. 405-409.

Yang et al., "Glycolipid Nanotube Hollow Cylinders as Substrates: Fabrication of One-Dimensional Metallic-Organic Nanocomposites and Metal Nanowires", Chem. Mater., vol. 16, 2004, pp. 2826-2831.

Yui et al., "Encapsulation of Ferritin within a Hollow Cylinder of Glycolipid Nanotubes", Chemistry Letters, vol. 34, No. 2, 2005, pp. 232-233.

O'Brien et al., "Reduced cardiotoxicity and comparable efficacy in a phase III trial of pegylated liposomal doxorubicin HCL (CAELYX™/Doxil®) versus conventional doxorubicin for first—line treatment of metastatic breast cancer", Annals of Oncology, vol. 15, 2004, pp. 440-449.

Masuda et al., "Lipid Nanotubes and Microtubes: Experimental Evidence for Unsymmetrical Monolayer Membrane Formation from Unsymmetrical Bolaamphiphiles", Langmuir, vol. 20, 2004, pp. 5969-5977.

Lee et al., "Fabrication of Metal Cation-Doped Nanotube by Using Unsymmetrical Bolaamphiphiles", Polymer Preprints, Japan, vol. 58, No. 2, 2009, 1 page.

Lee et al., "Molecular Monolayer Nanotubes self-assembled from Unsymmetrical Bolaamphiphiles Having 1-Glucosamide and Carboxy-Terminal Oligo-Glycine Headgroups", The 1st FAPS Polymer Congress, Poster No. 22PS2-006b, 2009, 1 page.

Kameta et al., "Self-assembled organic nanotubes embedding hydrophobic molecules within solid bilayer membranes", Soft Matter, vol. 7, 2011, pp. 85-90.

Chiku et al., "A novel protein refolding method using a zeolite", Analytical Biochemistry, vol. 348, 2006, pp. 307-314.

Akiyoshi et al., "Molecular Chaperone-Like Activity of Hydrogel Nanoparticles of Hydrophobized Pullulan: Thermal Stabilization with Refolding of Carbonic Anhydrase B", Bioconjugate Chemistry, vol. 10, No. 3, May/Jun. 1999, pp. 321-324.

Sasaki et al., "Polysaccharide nanogel-cyclodextrin system as an artificial chaperone for in vitro protein synthesis of green fluorescent protein", Polymer Journal, vol. 42, 2010, pp. 823-828.

Kameta et al., "Supramolecular Nanotube *endo* Sensing for a Guest Protein", Small, vol. 4, No. 5, 2008, pp. 561-565.

Lubineau et al., "Improved synthesis of glycosylamines and a straightforward preparation of *N*—acylglycosylamines as carbohydrate-based detergents", Carbohydrate Research, vol. 266, 1995, pp. 211-219.

Reinhard et al., "Tetranonacontane", Journal of Organic Chemistry, vol. 30, 1965, pp. 1450-1453.

Kameta et al., "Supramolecular Nanotube Hydrogels: Remarkable Resistance Effect of Confined Proteins to Denaturants", Chemistry of Materials, vol. 21, 2009, pp. 5892-5898.

Kameta et al., "Self-Assembly and Thermal Phase Transition Behavior of Unsymmetrical Bolaamphiphiles Having Glucose-and Amino-Hydrophilic Headgroups", Langmuir, vol. 23, 2007, pp. 4634-4641.

Kameta et al., "Molecular Monolayer Nanotubes Having 7-9 nm Inner Diameters Covered with Different Inner and Outer Surfaces", Chemistry Letters, vol. 36, No. 7, 2007, pp. 896-897.

* cited by examiner

ORGANIC NANOTUBE HAVING HYDROPHOBIZED INNER SURFACE, AND ENCAPSULATED MEDICINAL AGENT PREPARED USING THE NANOTUBE

TECHNICAL FIELD

The present invention relates to a hollow fibrous nanotube having a hydrophilized outer surface and a hydrophobized hollow cylinder inner surface (that is, an organic nanotube having a hydrophobized inner surface), a method of preparing thereof, a method of refolding denatured protein using the organic nanotube having a hydrophobized inner surface, a method of encapsulating a hydrophobic drug, and a sustained-release method and a control thereof.

BACKGROUND ART

A tubular structure, which is reversibly formed by self-assembly in water of accurately designed amphiphilic molecules, encapsulates a hydrophilic guest such as biopolymer, protein (natural state), DNA, various nanoparticles, as well as small molecules, into a hydrophilic hollow cylinder having an inner diameter of 5 to 100 nm. The tubular structure is easily dispersed in water due to outer and inner surfaces covered with a hydrophilic group. In addition, the tubular structure as described above controls storage and release of the encapsulated hydrophilic guest in response to external stimulation such as pH, temperature, light, additive, and thereby the tubular structure has been particularly paid attention in a biotechnological or medical field (Non-Patent Literature 1). It is expected to apply the tubular structure to an immobilization matrix or the like a storage capsule of proteins, or a drug delivery capsules, using characteristics of the tubular structure (Non-Patent Literatures 2 and 3). However, in most of the existing organic nanotubes, since inner and outer surfaces thereof were covered with the same hydrophilic portions, it was difficult to selectively and efficiently encapsulate a raw material such as a drug, protein in the organic nanotube (Non-Patent Literatures 4 to 6). In detail, during encapsulation of the raw materials, a complicated operation has been required such that removing water in the organic nanotube by freeze-drying under reduced pressure, or the like, and adding an aqueous solution in which the raw materials are dispersed and dissolved to thereby rehydrate the organic nanotube (so called capillary phenomenon) (Non-Patent Literatures 4 and 5).

The present inventors have, so far, developed a manufacturing technology of an organic nanotube (asymmetric organic nanotube), having a monolayer membrane structure in which inner and outer surfaces thereof are covered with respective hydrophilic groups, by self-assembly in water of asymmetric bipolar lipid molecules having two different hydrophilic groups at both ends of an hydrophobic alkylene chain (Patent Literature 1, and Non-Patent Literature 1). Recently, the present inventors developed and filed a patent for an asymmetric nanotube capable of slowly releasing a drug and having characteristics as an excellent drug capsule by encalulating an amino amino-group containing drug such as doxorubicin, using an asymmetric bipolar lipid molecules in which 2-glucosamine and oligo glycine moieties are linked to both ends of long chain dicarboxylic acid via amide bonds, respectively (Japanese Patent Application No. 2010-194544). Since a functional group capable of interacting with a hydrophilic guest may be site-specifically localized on the inner surface of the asymmetric organic nanotube, the hydrophilic guest may be selectively and efficiently encapsulated in a hollow cylinder of the asymmetric organic nanotube. In addition, release of the hydrophilic guest into the bulk may be controlled by applying external stimulus to reduce interactions between the inner surface of the asymmetric organic nanotube and the hydrophilic guest. For example, a small molecule, oligo DNA, double stranded DNA, protein, nanoparticles, or the like may be selectively and efficiently encapsulated as an anionic and hydrophilic guest in a hollow cylinder having a cationic property by protonation of an amino group localized on the inner surface of the asymmetric nanotube. The encapsulated hydrophilic guest may be sustainably released into the bulk by applying external stimulus to change a pH in a solution so as to perform deprotonation of the amino group on the inner surface of the asymmetric organic nanotube.

It has been demanded to develop an encapsulant capable of encapsulating the drug simply and efficiently, maintaining stably, and continuously releasing a drug in target cells of lesions such as cancer cells or tissue. Particularly, since anthracycline based anticancer agents, such as doxorubicin, idarubicin, epirubicin, daunorubicin, pirarubicin, widely used for treating cancer have strong toxicity, particularly, cardiac toxicity, it has been demanded to develop an excellent encapsulant capable of directly and effectively delivering the anticancer agent to cancer cells and sustainably-releasing the anticancer agent. In addition, in view of reducing an administration frequency or dose of a drug to thereby reduce burden of patients, it has been urgently demanded to develop a technology of controlling a sustained-release rate of a drug.

In the case of a liposome based drug nanocapsules (Non-Patent Literature 7) prepared in this regard, since a pH gradient was used, subsequent purification was required. Therefore, preparation was complicated and required a long period of time.

In contrast, the asymmetric nanotube, developed by the present inventors (Japanese Patent Application No. 2010-194544, or the like), has a carboxylic-acid inner surface, and is thereby-capable of encapsulating a hydrophilic guest including the amino group-containing drug doxorubicin, or the like in a hollow cylinder by mixing the nanotube and the drug in water because the nanotube has a carboxylic-acid inner surface. In addition, the asymmetric nanotube has a sustained-release function depending on a change in environmental pH. Therefore, the asymmetric nanotube is effectively applied as a drug capsule.

However, in the case of the asymmetric nanotube according to the related art developed by the present inventors, there was no method of precisely controlling a sustained-release property of the encapsulated drug under physiological conditions. In addition, since there was a problem in stability of the tube itself as describe below, a precisely controlling the sustained-release was not yet achieved.

Particularly, in a carboxylic acid based asymmetric bipolar lipid group according to the related art, the resultant asymmetric nanotube was slowly changed into another morphology, such that a sustained-release property of the drug was lost after being exposed for only 2 hours or for at most about 12 hours under physiological conditions. More particularly, an asymmetric nanotube (Non-Patent Literature 8) formed by lipid molecules in which a 1-glucopyranosyl group was bonded at one end of long chain dicarboxylic acid via an amide bond was slowly changed, under the physiological conditions (for example, PBS buffer, pH 7.5), into a microtube having an outer diameter of 120 to 200 nm, an acicular crystal, or the like, after about 4 hours. Further, during a manufacturing process of the asymmetric nanotube according to the related art, since microtubes or tape-like assemblies were simultaneously formed, a separation and purification process of the nanotube by centrifugation, or the like, has been required. In addition, there were problems in that at the time of long term preservation at room temperature or a cold temperature, the asymmetric nanotube may be easily crystallized, and long term preservation stability was not high.

A development of asymmetric bipolar lipid molecules in which mono- and di-glycine residues are introduced at a carboxylic acid terminus of the carboxylic acid based lipid molecule enabled us to solve these problems described above, such as lack of long term preservation stability of the nanotubes, and requirement of separation and purification process (Non-Patent Literatures 9 and 10). Further, asymmetric nanotubes formed by these lipid molecules were able to improve a long-term preservation property. However, in these asymmetric nanotubes, there was a problem such that after being exposed under physiological conditions (PBS buffer, pH 7.5), an inner diameter of the nanotube was changed from about 7 nm into about 50 nm (it will be described below in Example 5).

Even in an asymmetric organic nanotube (Japanese Patent Application No. 2010-194544) recently developed by the present inventors, the problem such that after being exposed under physiological conditions for several hours, a structure of the asymmetrical nanotube was changed into a fibrous structure was not solved. Hence, a sustained-release property at the time of administering the nanotube to a body as a drug capsule should be further improved, and it is necessary to precisely control the sustained-release.

In addition, as described above, since a target drug in a delivery system for directly delivering the drug to the lesion site, such as the anticancer drugs including doxorubicin, or the like, often has high hydrophobicity, it is necessary to use an encapsulant capable of delivering a hydrophobic guest to the lesion site and slowly releasing the hydrophobic guest in the lesion site.

As a technology of encapsulating a hydrophobic molecule according to the related art, only in the case of a hydrophobic small molecule capable of being encapsulated in a cyclodextrin hollow pore having a size of about 1 nm, the hydrophobic small molecule may be encapsulated in a hydrophilic hollow cylinder of an organic nanotube formed by amphiphilic molecules and released in water by forming a complex with cyclodextrin (Patent Literature 2). However, in order to prepare the complex, a complicated process was required, and a yield thereof was low. In addition, since the organic nanotube disclosed in the corresponding document has a bilayer structure, inner and outer surfaces thereof are covered with the same hydrophilic group. Thus, the cyclodextrin complex may not be selectively encapsulated in the hollow cylinder. Further, since there is no specific interaction between the inner surface of the hollow cylinder and the cyclodextrin complex, it is impossible to control release.

An intercalated-type organic nanotube which are able to decentrally embed hydrophobic small molecules having a size of 1 to 3 nm in a membrane wall of the organic nanotube was developed (Patent Literature 3). The hydrophobic small molecules may be embedded at a content of 10% based on substrate lipid molecules and dispersed in water while maintaining a shape of the organic nanotube. However, in order to allow the hydrophobic small molecules embedded in the membrane wall to be released, the organic nanotube should be decomposed using an additive, or the membrane wall should be changed in a fluid state by heating the organic nanotube at a gel-liquid crystal phase transition temperature or more (Non-Patent Literature 11). In this case, the hydrophobic small molecules may be relatively rapidly released.

Although an organic nanotube of which all of the inner and outer surfaces are covered with a hydrophobic group was developed, hydrophobic small molecules, hydrophobic nanoparticles, or the like, are adsorbed in the inner and outer surfaces, but they are mainly adsorbed in the outer surface (Patent Literature 4), thus this organic nanotube may not disperse hydrophobic molecules in water.

As described above, various fields have been, therefore, urgently demanded to develop an organic nanotube which has a hydrophilized outer surface and a hydrophobized outer surface, capable of having a sufficient space in a hydrophobic hollow cylinder, enabling direct interaction between the inner surface and a hydrophobic guest, and capable of releasing the hydrophobic guest while maintaining a shape of the organic nanotube which has not yet been implemented. If the organic nanotube as described above is constructed, it will be possible to selectively encapsulate a hydrophobic polymer and a hydrophobic nanostructure as well as a hydrophobic small molecule in the hollow cylinder to disperse the encapsulated material in water. In addition, unlike the related art (Patent Literature 2), since the inner surface of the nanotube and the hydrophobic guest may directly interact with each other, if the interaction is suppressed through external stimulus, release control is possible. Further, the hydrophobic guest may be released even without decomposing the organic nanotube or making the membrane wall to be in a fluid state as in the related art (Patent Literature 3).

In addition, the above-described asymmetric organic nanotube (Japanese Patent Application No. 2010-194544) recently developed by the present inventors, in the case of using hydrophobic guests, for example, a drug having high hydrophobicity such as doxorubicin, a sufficient sustained-release property was not obtained, and in view of precisely controlling the sustained-release, the asymmetric organic nanotube was not sufficient.

However, it also has been demanded to develop, with regard to encapsulation of hydrophobic molecules, an efficient method of refolding genetic recombinant protein, or the like.

That is, it has been urgently demanded, in view of industrial mass-production of normal protein, to develop a material having a nano space for encapsulating of protein in which hydrophobic groups are partially exposed by denaturation (denatured protein). β-zeolite, which is a porous inorganic material, may adsorb denatured protein (Non-Patent Literature 12). It was reported that protein was separated from β-zeolite by cleaning a denaturant and adding a buffer solution containing polyethylene glycol or surfactant to thereby be recovered (refolded) to have a normal structure. In addition, an amphiphilic polymer in which a cholesteryl group as a hydrophobic group is introduced in polysaccharide, which is a hydrophilic polymer, may be self-assembled in water to form a gel (nanogel) having a size of 20 to 30 nm (Non-Patent Literature 13). It was reported that the denatured protein was encapsulated in the inner space of the nanogel, then release and refolding of protein were simultaneously occurred when the nanogel was collapsed by adding cyclodextrin (Non-Patent Literature 14). However, a protein solution obtained from the β-zeolite and the nanogel includes polyethylene glycol, or the surfactant, cyclodextrin, and a composite polymer of cyclodextrin and hydrophobized polysaccharide, and a complicated separation process for removing other components except for the protein is required.

Therefore, it has been strongly expected to develop an organic nanotube of which only an inner surface of a hollow cylinder portion thereof is hydrophobized (an organic nanotube having a hydrophobized inner surface) in order to solve all problems as described above. That is, it has been urgently demanded to develop the organic nanotube having a hydrophobized inner surface capable of selectively and efficiently encapsulating denatured protein as a hydrophobic guest, having a function of assisting in refolding, and releasing normal protein without adding a specific additive. In addition, it has been urgently demanded to develop the organic nanotube having a hydrophobized inner surface capable of selectively and efficiently encapsulating a drug such as doxorubicin as a hydrophobic guest and sustainably-releasing the drug into a bulk according to the external environment.

Particularly, in controlling sustainable-release of the drug, it has been strongly expected to provide an asymmetric nanotube capable of maintaining a tubular structure for a long period of time even under any physiological conditions (for example, in PBS buffer at pH 7.5 and 35° C.) while maintaining the existing excellent properties of stable carboxylic acid based asymmetric nanotube groups having an inner surface covered with a carboxylic group, and a new asymmetric bipolar lipid molecule for the asymmetric nanotube. That is, it has been urgently demanded to provide an asymmetric bipolar lipid molecule capable of manufacturing a nanotube capsules with excellent properties as follows: selectively and efficiently preparing an asymmetric nanotube with a high yield under mild conditions; having long-term preservation stability in the obtained asymmetric nanotube; efficiently encapsulating a cationic drug such as doxorubicin at a high concentration; and having stable morphology of the tube under physiological conditions.

CITATION LIST

Patent Literature

[Patent Literature 1] Japanese Patent No. 4174702
[Patent Literature 2] Japanese Patent Laid-Open Publication No. 2009-136975
[Patent Literature 3] Japanese Patent Laid-Open Publication No. 2008-264897
[Patent Literature 4] Japanese Patent Laid-Open Publication No. 2010-005706

Non-Patent Literature

[Non-Patent Literature 1] Kameda et al., Proceedings of Polymer, 67, 560 (2010).
[Non-Patent Literature 2] Chia-Chun, C. et al., Advanced Materials, 17, 404 (2005).
[Non-Patent Literature 3] Martin, C. et al., Adv. Mater., 18, 405 (2006).
[Non-Patent Literature 4] Shimizu, T. et al., Chem. Mater., 16, 2826 (2004).
[Non-Patent Literature 5] Yui, H. et al., Chem. Lett., 34, 232 (2005).
[Non-Patent Literature 6] "Application technology of annular-cylindrical supramolecular new material", edited by Takada Tosicaze, CMC Publications, Tokyo, P138-149 (2006).
[Non-Patent Literature 7] O'Brien, M. E., Ann. Oncol., 15, 440 (2004).
[Non-Patent Literature 8] Masuda, M. et al., Langmuir, 20, 5969 (2004).
[Non-Patent Literature 9] Lee, S. J., The 58th polymer science Congress, Announcement No. 1Pe047 (2009).
[Non-Patent Literature 10] Lee, S. J., The 1st FAPS Polymer Congress, Abstract, (Nagoya), Poster No. 22PS2-006b (2009).
[Non-Patent Literature 11] Kameta, N. et al., Soft Matter, 7, 85 (2011).
[Non-Patent Literature 12] Mizukami, F., Anal. Biochem., 348. 307 (2006).
[Non-Patent Literature 13] Akiyoshi, K., Bioconj. Chem., 10, 321 (1999).
[Non-Patent Literature 14] Akiyoshi, K., Polym. J., 42, 823 (2010).
[Non-Patent Literature 15] Kameta, N., et al., Small, 4, 561 (2008).
[Non-Patent Literature 16] Lubineau, A., Carbohydr. Res., 266, 211 (1995).
[Non-Patent Literature 17] Reinhard, R. R., J. Org. Chemistry, 30, 1450 (1965).
[Non-Patent Literature 18] Kameta, N. et al., Chem. Mater., 21, 5892 (2009).
[Non-Patent Literature 19] N. Kameta et al., Langmuir 23, 4634 (2007).
[Non-Patent Literature 20] N. Kameta et al., Chem. Lett. 36, 896 (2007).

SUMMARY OF INVENTION

Technical Problem

An object of the present invention is to provide an organic nanotube of which an outer surface is hydrophilic and only an inner surface of a hollow cylinder portion is hydrophobized (an organic nanotube having a hydrophobized inner surface). Another object of the present invention is to provide an organic nanotube having a hydrophobized inner surface capable of selectively, and efficiently encapsulating denatured protein, having a function of assisting in refolding, and releasing normal protein without adding a specific additive, being capable of encapsulating a hydrophobic drug such as doxorubicin at a high concentration, and having a sustained-release function according to the change in hydrophobicity of the inner surface or external stimulus and an encapsulation composition. Still another object of the present invention is to provide a new asymmetric bipolar lipid molecule capable of maintaining a stable tube structure under physiological conditions, and forming an asymmetric nanotube of which an inner surface thereof is covered with a mixture of a carboxylic group and ester thereof or a hydrophobic amide derivative. The other object of the present invention is to cause asymmetric bipolar lipid molecules to form an asymmetric nanotube capable of efficiently encapsulating a cationic drug such as doxorubicin at a high concentration and sustainably-releasing the drug without damaging a tube structure under physiological condition.

The present inventors have reported that binary self-assembly of an asymmetric bipolar lipid molecule having a 1-glucopyranosyl residue and an oligo glycine residue at both ends of a hydrophobic methylene chain as a hydrophilic part and a derivative obtained by connecting a hydrophilic fluorescent probe Alexa to an amino group of the oligo glycine end (Non-Patent Literature 15). As a result, the self-assembly gave an asymmetric organic nanotube having an outer surface covered with a 1-glucopyranosyl group and an inner surface covered with an oligo glycine amino group, and Alexa was formed by.

The present inventors newly found that an organic nanotube having a hydrophobic functional group localized on only an inner surface (an organic nanotube having a hydrophobized inner surface) may be formed by binary self-assembly of an asymmetric bipolar lipid molecule represented by the following General Formula (1) and a derivative having the hydrophobic functional group at the end thereof and represented by General Formula (2).

As compared to an organic nanotube formed using only the molecule represented by the following General Formula (1), the organic nanotube having a hydrophobized inner surface had a higher encapsulation rate of denatured protein of which hydrophobic groups are exposed into a hollow cylinder and higher refolding efficiency. It was possible to release this normal protein in the hollow cylinder into bulk water by pH stimulation without requiring an additive (refolding function).

In addition, it was found that the organic nanotube having a hydrophobized inner surface can encapsulate more hydrophobic drugs, as compared to an organic nanotube formed using only the molecule represented by the following General Formula (1), and release the hydrophobic drug encapsulated in the hollow cylinder into bulk water by a pH change of a dispersion solution. Surprisingly, a sustained-release property of a hydrophobic drug is controllable by changing ratio between the molecules represented by General Formulas (1) and (2) to change hydrophobicity of the inner surface (function of controlling the sustained-release property of the hydrophobic drug).

Further, in asymmetric bipolar lipid molecules (Non-Patent Literatures 9 and 10) including oligo glycine composed of 1 or 2 residues, and the lipid molecule having the glucopyranosyl group at one end of a hydrophobic alkyl chain having a length equal to or longer than that of an octadecamethylene chain and having carboxylic acid at the other end thereof among asymmetric bipolar lipid molecules configuring the nanotube having a hydrophobized inner surface and represented by General Formula (1) and esters thereof, a new asymmetric bipolar lipid molecule in which the number of oligo glycine residues was further increased up to 3 to 6 was synthesized. It was found that this new asymmetric bipolar lipid molecule may form a carboxylic acid-based asymmetric nanotube by self-assembly thereof similarly to the asymmetric bipolar lipid molecule according to the related art, and stability of a tubular structure may be significantly increased under physiological conditions. Particularly, the carboxylic acid based asymmetric nanotube maintained a stable tubular structure even under the physiological conditions for 32 hours or more. It was confirmed that even in the case of substituting carboxylic acid at the end of the asymmetric bipolar lipid molecule with ester such as methyl ester, the stable asymmetric nanotube may be similarly formed.

In addition, the asymmetric bipolar lipid molecule may form the asymmetric nanotube even in the case of having a free carboxylic group at the end thereof, the case of having an ester group, and the case of being mixed or not mixed. In this carboxylic acid based asymmetric nanotube, efficiency of encapsulating a drug was significantly increased. Even as compared to the carboxylic acid base asymmetric nanotube (Japanese Patent Application No. 2010-194544) previously developed by the present inventors, efficiency of encapsulating doxorubicin in milli Q water was improved from 75% to 95% or more when pH was 6.5 and a ratio of the nanotube to doxorubicin was 5:1. Accordingly, it was possible to quantitatively encapsulate the drug (FIG. 18), and a sustained-release property under physiological conditions were significantly excellent (FIG. 19).

Further, this asymmetric nanotube under an acidic condition (pH 5.5) had a characteristic of releasing a drug at a rate at least twice the rate in a neutral condition (pH 7.4). Therefore, considering that cancer tissue is acidic (pH 6.5) as compared to other normal tissue, it is expected that, in the case of using this asymmetric nanotube as a drug capsule for anti-cancer agent, selective release of the drug in the cancer tissue.

More specifically, the present invention will be described as follows.

[1] There is provided an organic nanotube having a hydrophobized inner surface including an asymmetric bipolar lipid molecule represented by the following General Formula (1), and a derivative thereof represented by the following General Formula (2), and formed by binary self-assembly;

[Chemical Formula 1]

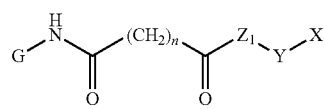

General Formula (1)

[Chemical Formula 2]

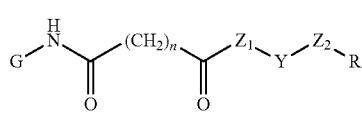

General Formula (2)

In Formulas (1) and (2), the same symbols have the same meanings, and G is a 1-glucopyranosyl group or 2-glucopyranosyl group.

n is an integer of 12 to 22.

$Z_1$ and $Z_2$ is a single bond or

[Chemical Formula 3]

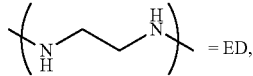 = ED, and when $Z_1$ is ED, $Z_2$ is be a single bond.

Y is

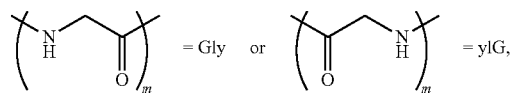

m is be an integer of 2 to 6, and

X is OH when Y is Gly and is H when Y is ylG.

R is a benzyloxycarbonyl group, a t-butoxycarbonyl group, a 9-fluorenylmethoxycarbonyl group, an acetyl group, an ethylcarbonyl group, a propylcarbonyl group, an alkoxy group having 1 to 4 carbon atoms, a benzyloxy group, or hydrophobic amino acid.

[2] There is provided the organic nanotube having a hydrophobized inner surface of [1], in which R is a methoxy group, an ethoxy group, or a t-butoxy group among alkoxy groups having 1 to 4 carbon atoms, or alanine, valine, leucine, isoleucine, methionine, proline, phenylalanine, or tryptophan among the hydrophobic amino acids.

[3] There is provided the organic nanotube having a hydrophobized inner surface of [1], in which in General Formulas (1) and (2), wherein n is an integer of 18 to 22, both of $Z_1$ and $Z_2$ are single bonds, Y is Gly, m(s) are the same or different integer of 3 to 6, X is OH, and R is a methoxy, ethoxy, or benzyloxy group, and in which the organic nanotube is a carboxylic acid-based asymmetric nanotube formed from asymmetric bipolar lipid molecules each represented by following General Formulas (5) and (6), and;

[Chemical Formula 7]

General Formula (5)

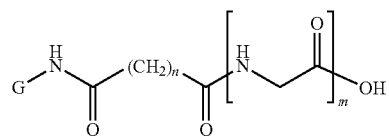

(wherein, n is an integer of 18 to 22, and m is an integer of 3 to 6).

[Chemical Formula 8]

General Formula (6)

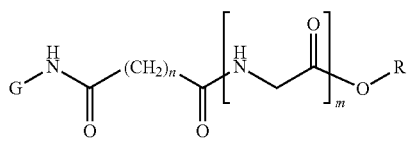

(wherein, n has the same meaning as that of General Formula (1), m indicates the same or different integer of 3 to 6, and R indicates a straight chain alkyl group having 1 to 4 carbon atoms).

[4] There is provided an asymmetric bipolar lipid molecule, a salt thereof, or an ester thereof represented by the following General Formulas (5) and (6);

[Chemical Formula 7]

General Formula (5)

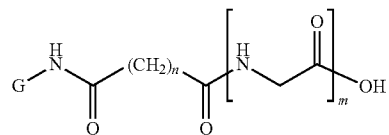

(wherein, n is an integer of 18 to 22, and m is an integer of 3 to 6).

[Chemical Formula 8]

General Formula (6)

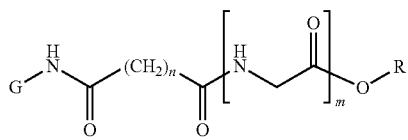

(wherein, n has the same meaning as that of General Formula (5), m indicates the same or different integer of 3 to 6, and R indicates a straight chain alkyl group having 1 to 4 carbon atoms).

[5] There is provided a carboxylic acid based asymmetric nanotube formed by self-assembly of any one of the asymmetric bipolar lipid molecules of [4], salts thereof, and esters thereof, or a mixture thereof.

[6] There is provided a method of preparing an organic nanotube having a hydrophobized inner surface, the method including mixing the asymmetric bipolar lipid molecules represented by General Formula (1) and the derivative represented by General Formula (2) in an aqueous solvent to perform binary self-assembly to form the organic nanotube of any one of claims [1] to [3] and [5].

[7] There is provided a method of preparing a carboxylic acid based asymmetric nanotube, the method including dispersing a asymmetric bipolar lipid molecule or an ester thereof represented by General Formula (5) or (6) alone or dispersing a mixture thereof in dimethylsulfoxide, dimethylformamide, or water, and heating the resultant so as to be dissolved, and then cooling the resultant.

[Chemical Formula 7]

General Formula (5)

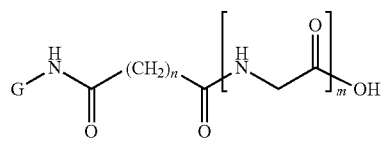

(wherein, n is an integer of 18 to 22, and m is an integer of 3 to 6).

[Chemical Formula 8]

General Formula (6)

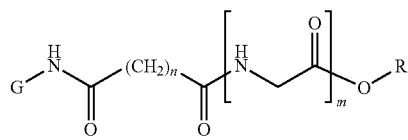

(wherein, n has the same meaning as that of General Formula (1), m indicates the same or different integer from 3 to 6, and R indicates a straight chain alkyl group having 1 to 4 carbon atoms).

[8] There is provided a protein refolding agent including the organic nanotube having a hydrophobized inner surface of [1] or [2] as an active component.

[9] There is provided a method of refolding denatured protein including the denatured protein encapsulated in the organic nanotube having a hydrophobized inner surface of [1] or [2] by dispersing the denatured protein and the organic nanotube in an aqueous solvent.

[10] There is provided the method of refolding of [9], further including adding the denatured protein into an aqueous medium at the time of mixing the asymmetric bipolar lipid molecule and the derivative to perform the binary self-assembly.

[11] There is provided a composition for releasing refolded normal protein, in which the denatured protein is encapsulated in a hydrophobic hollow cylinder of the organic nanotube having a hydrophobized inner surface of [1] or [2].

[12] There is provided a sustained-release encapsulated formulation of a hydrophobic drug including the organic nanotube having a hydrophobized inner surface of [1] to [3], or [5] as an active component.

[13] There is provided a method of encapsulating a hydrophobic drug, the method including encapsulating the hydrophobic drug in an organic nanotube having a hydrophobized inner surface of any one of [1] to [3], and [5] by dispersing the hydrophobic drug and the organic nanotube in an aqueous solvent.

[14] There is provided the method of encapsulating of [13] further including adding the hydrophobic drug into an aqueous medium at the time of mixing the asymmetric bipolar lipid molecule and the derivative to perform the binary self-assembly.

[15] There is provided an encapsulated hydrophobic drug in which a hydrophobic drug is encapsulated in a hydrophobic hollow cylinder of the organic nanotube having a hydrophobized inner surface of [1] to [3], or [5].

[16] There is provided the sustained-release formulation of a hydrophobic drug of [12], in which the formulation is for a sustained-release formulation of a cationic drug including the carboxylic acid-based asymmetric nanotube of [3] or [5] as an active component.

[17] There is provided the encapsulated hydrophobic drug composition of [15], in which the carboxylic acid-based asymmetric nanotube of [3] or [5] encapsulates a cationic drug to form a cationic drug-asymmetric nanotube complex.

[18] There is provided a cationic drug-asymmetric nanotube complex, in which the carboxylic acid based asymmetric nanotube of [3] or [5] encapsulates a cationic drug.

[19] There is provided a cationic drug composition including the cationic drug-asymmetric nanotube complex of [18] as an active component.

[20] There is provided the cationic drug in which the cationic drug is an anthracycline based anticancer agent having an amino group.

Advantageous Effects of Invention

According to the present invention, it is possible to establish a method of forming "an organic nanotube having a hydrophobized inner surface", which is an organic nanotube having only an inner surface hydrophobized, by binary self-assembly with a yield of 100% and in a simplified manner. The organic nanotube having a hydrophobized inner surface can also controllably perform encapsulation, storage, and release on a guest including from a hydrophobic small molecule to a polymer as a target and also have a function of refolding denatured protein into normal protein. Particularly, it can be expected that denatured protein and doxorubicin, which is an anticancer agent, or the like, as a target of the guest would make the organic nanotube having a hydrophobized inner surface applied to a next generation artificial molecular chaperone system or a next generation drug delivery system. The present invention is important in cosmetic or other functional material fields requiring water dispersion and sustained-release functions of a hydrophobic material as well as biotechnical or medical fields.

In addition, according to the present invention, an asymmetric nanotube capable of stably maintaining a tube shape for a long period of 30 hours or more even at a high salt condition under such a physiological conditions (pH 7.4, in PBS buffer) can be prepared, which was difficult in a "carboxylic acid based asymmetric nanotube" having an inner surface covered with a carboxylic group and an outer surface covered with a sugar residue.

The carboxylic acid based asymmetric nanotube according to the present invention has a high dispersibility in water, an aqueous solvent, or an organic solvent. Even though the carboxylic acid based asymmetric nanotube is present in the aqueous solvent at a high concentration, crystallization is not occurred, and long-term preservation stability is significantly high, such that the carboxylic acid based asymmetric nanotube can be stably preserved for 2 months or more in a water dispersion solution at a relatively high concentration of 5 mg/ml. Further, an asymmetric bipolar lipid molecule configuring this asymmetric nanotube is a new compound, and raw materials thereof, that is, β-D-glucopyranosylamine, long-chain dicarboxylic acid, and oligo glycines are inexpensive. For example, in General Formula (1), wherein G is a 1-glucopyranosyl group, u is an integer of 18 to 22, $Z_1$ is a single bond, Y is Gly, and m is an integer of 3 to 6, the asymmetric bipolar lipid molecule can be prepared by a 5-step synthetic reactions under mild conditions without using column chromatography for purification, and high purity lipid can be obtained by only a reprecipitation process. Similarly, in the case of a compound of General Formula (2) (wherein G is a 1-glucopyranosyl group, n is an integer of 18 to 22, $Z_1$ and $Z_2$ are single bonds, Y is Gly, m is an integer of 3 to 6, and R is an alkoxy group having 1 to 4 carbon atoms or benzyloxy group) corresponding to an ester derivative of General Formula (1), the asymmetric bipolar lipid molecule can be similarly prepared by a 4-step synthetic reaction. Accordingly, this simple synthesizing and purification of the asymmetric nanotube-forming bipolar lipid molecule and simple preparation of the asymmetric nanotube in mild conditions are important in synthesizing a capsule as a drug carrier on a large scale and decreasing a cost of a final drug composition.

In addition, long-term preservation stability of the carboxylic acid based asymmetric nanotube and an excellent dispersibility at a high concentration are essential for securing safety of each drug and decreasing the entire amount of a liquid intravenously administered in order to reduce burden of patients in chemotherapy. In addition, the organic nanotube having a hydrophobized inner surface and the carboxylic acid based asymmetric nanotube according to the present invention have an diameter of only 15 nm, and a length thereof can be controlled at about 100 nm to 10 μm by changing a condition of self-assembly. Therefore, an amount of the tube delivered to cancer tissue can be increased by an enhanced permeability and retention (EPR) effect. As described above, the stability or excellent dispersibility of the asymmetric nanotube according to the present invention is one of the excellent properties as a drug carrier.

In addition, since the inner surface of the carboxylic acid based asymmetric nanotube according to the present invention or some of the nanotubes having a hydrophobized inner surface is at least partially covered with the carboxylic group to thereby have a negative charge at a pH near neutral, encapsulation of drug can be performed only by mixing a drug having an amino group such as doxorubicin or a cationic drug with this nanotube. In the case of a conventional liposome-based drug capsule having a complicated preparation process, it was impossible to mix the drug capsule at an arbitrary ratio at the time of treatment, and only a drug encapsulated in advance was sold on the market. However, according to the present invention, encapsulation can be performed by rapidly adjusting the nanotube as a drug capsule in a medical practice or mixing a nanotube dispersion solution and a drug at an arbitrary ratio at the time of treatment. As described above, since lipid synthesis of the raw material or preparation of the nanotube is significantly easy, the asymmetric nanotube according to the present invention can be provided as an inexpensive drug capsule.

In addition, the asymmetric nanotube according to the present invention can sustainably release the encapsulated drug from pores of both ends of the tube while not changing its shape under the physiological conditions. Further, in a low pH environment, a degree of ionization of the carboxylic group covering the inner surface of the tube is decreased, which weakens an electrostatic interaction with a cationic drug, so that the drug can be efficiently released. Therefore, efficient release of the drug in the low pH environment peculiar to cancer tissue in addition to selective delivery of the nanotube to the cancer tissue by the EPR effect can be performed. Further, in the case of a nanotube complex injected into cancer cells, rapid release of the drug can be performed due to a low pH environment in endosome.

In view of a structure, there is not much almost no difference between the asymmetric bipolar lipid molecule (Non-Patent Literature 9) previously reported by the present inventors and the carboxylic acid based asymmetric bipolar lipid molecule according to the present invention, excepting that a length of an alkyl chain of the asymmetric bipolar lipid molecule is almost equal to (n=18) or slightly shorter than (n=14 or 16) than that of the carboxylic acid based asymmetric bipolar lipid molecule and the number of glycine residues is smaller (m=1 or 2). Manufacturing processes and organization process into the nanotube are, therefore, almost equal to each other, and shapes of the obtained asymmetric nanotubes are significantly similar to each other. Although the asymmetric nanotubes were similar to each other as described above, when the conventional asymmetric nanotube was left under physiological conditions, an inner diameter thereof was rapidly changed from about 7 nm to 50 nm and an outer diameter thereof was rapidly changed from about 15 nm to 100 to 150 nm within 1 hour, the encapsulated guest was instantly released, the sustained-release property was not implemented, and it was impossible to control a release rate.

a) Mixing ratio, Compound-1c of Formula (1): Compound-2e of Formula (2)=10:2 b) Mixing ratio, Compound-1c of Formula (1): Compound-2e of Formula (2)=10:10

Figure 7:
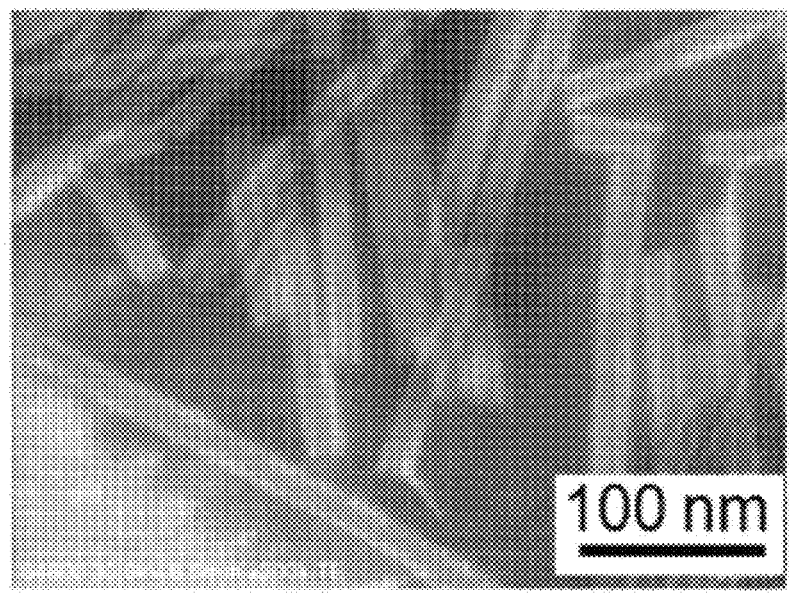
Figure 7:
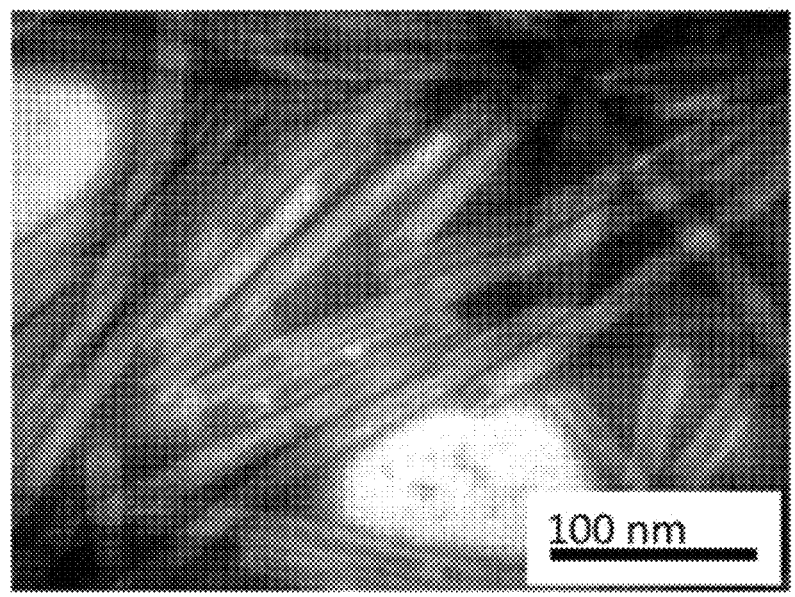

FIG. 7 is photographs showing electron microscopic images (transmission images) of an asymmetric nanotube obtained via self-assembly by heating and cooling Compound 1 in dimethyl sulfoxide (DMSO) (upper image: Compound-1c of Formula (1) (G=1-β-D-glucopyranosyl group, n=18, $Z_1$=single bond, Y=Gly, m=4, and X=OH), lower image: Compound-1d of Formula (1) (G=1-β-D-glucopyranosyl group, n=18, $Z_1$=single bond, Y=Gly, m=6, and X=OH)).

Figure 8:
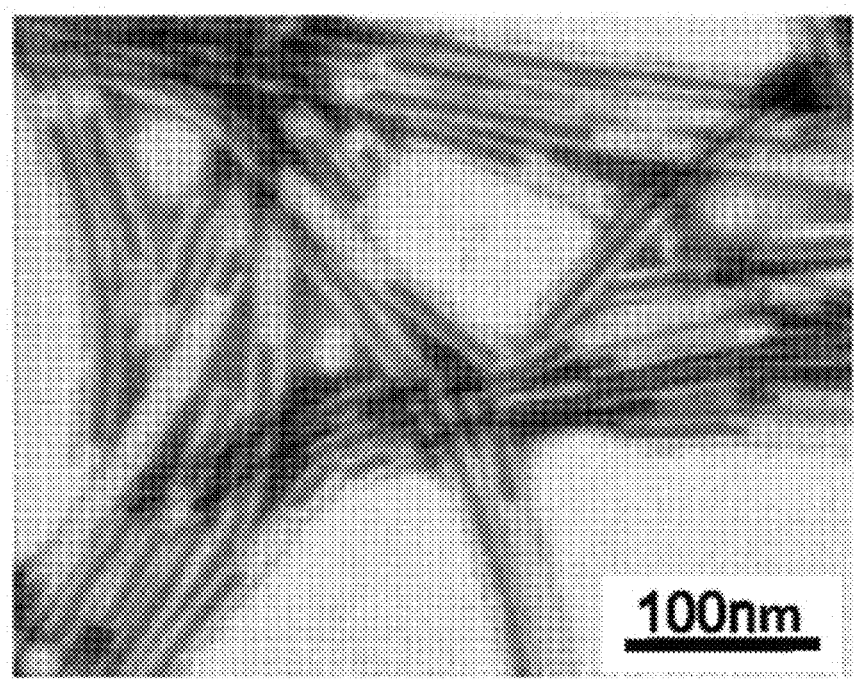

FIG. 8 is a photograph showing an electron microscopic image (transmission image) of an asymmetric nanotube obtained by self-assembly caused by heating and cooling an asymmetric bipolar lipid molecule (Compound-2c of Formula (2): G=1-β-D-glucopyranosyl group, $Z_1$=single bond, Y=Gly, m=4, $Z_2$=single bond, and R=methoxy group) in DMSO.

Figure 9:
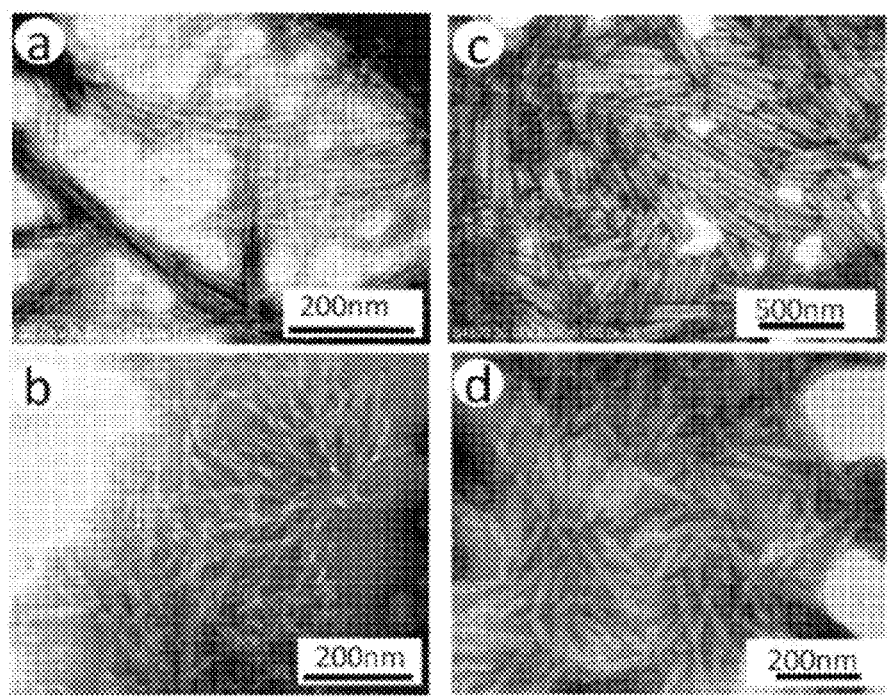

FIG. 9 are photographs showing evaluation of stability of the asymmetric nanotube at the time of incubating the asymmetric nanotube for 32 hours under physiological conditions, and comparison of the asymmetric nanotubes according to the present invention and the related art in electron microscope observation (transmission) images.

(a) In the case of "prior application nanotube A", most of the nanotubes are being changed into a fibrous morphology.

(b) In the case of "prior application nanotube B", similar results are obtained.

(c) Change of "conventional nanotube C": The morphology is changed into a large tube structure having an inner diameter of about 50 nm and an outer diameter of about 100 to 150 nm.

(d) Change of a symmetric nanotube prepared using Compound-1c of Formula (1) according to the present invention: The asymmetric nanotube structure is being maintained.

Figure 10:
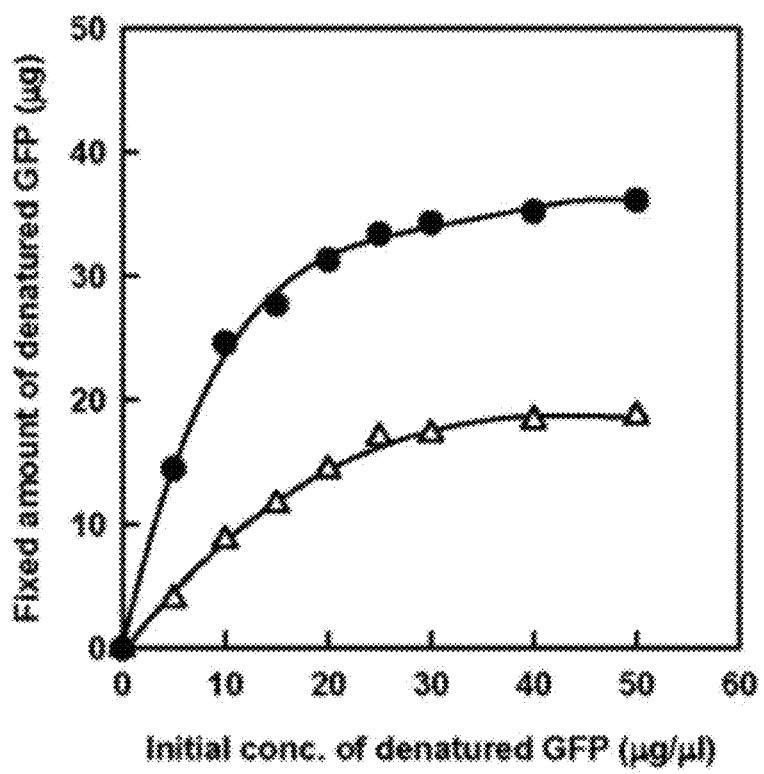

FIG. 10 is a graph showing a relationship between an initial concentration of denatured green fluorescent protein (GFP) and a concentration of denatured GFP encapsulated in an organic nanotube (5 mg). In the graph, ● indicates an organic nanotube having a hydrophobized inner surface formed by Compound-1a of Formula (1) and Compound-2a of Formula (2), and ▲ indicates an organic nanotube having a non-hydrophobized inner surface formed by Compound-1a of Formula (1).

Figure 11:
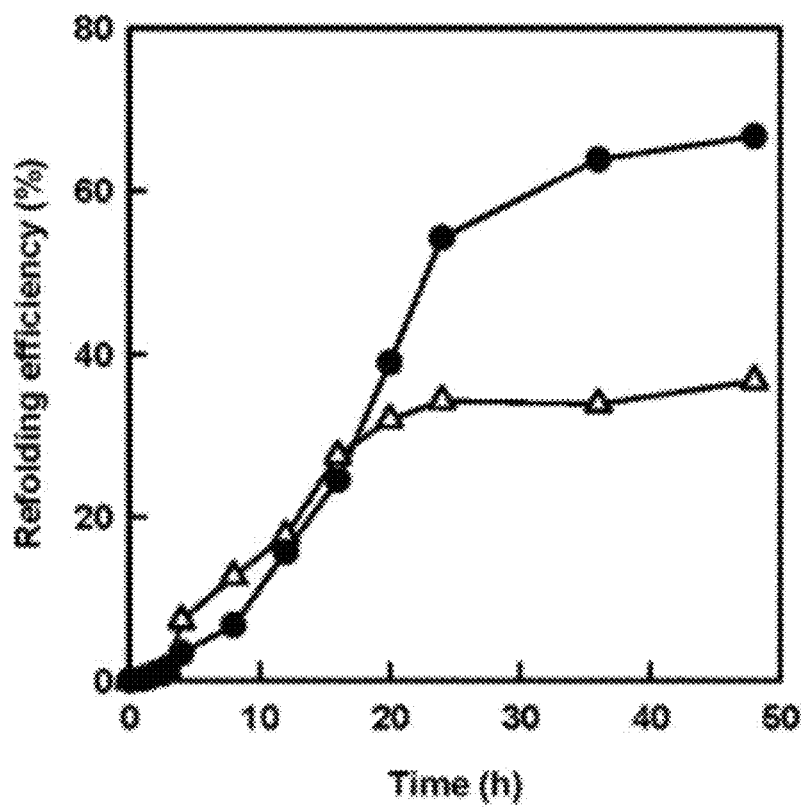

FIG. 11 is a graph showing refolding efficiency of denatured GFP encapsulated in the organic nanotube. In the graph, ● indicates an organic nanotube having a hydrophobized inner surface formed by Compound-1a of Formula (1) and Compound-2a of Formula (2), and Δ indicates an organic nanotube having a non-hydrophobized inner surface formed by Compound-1a of Formula (1).

Figure 12:
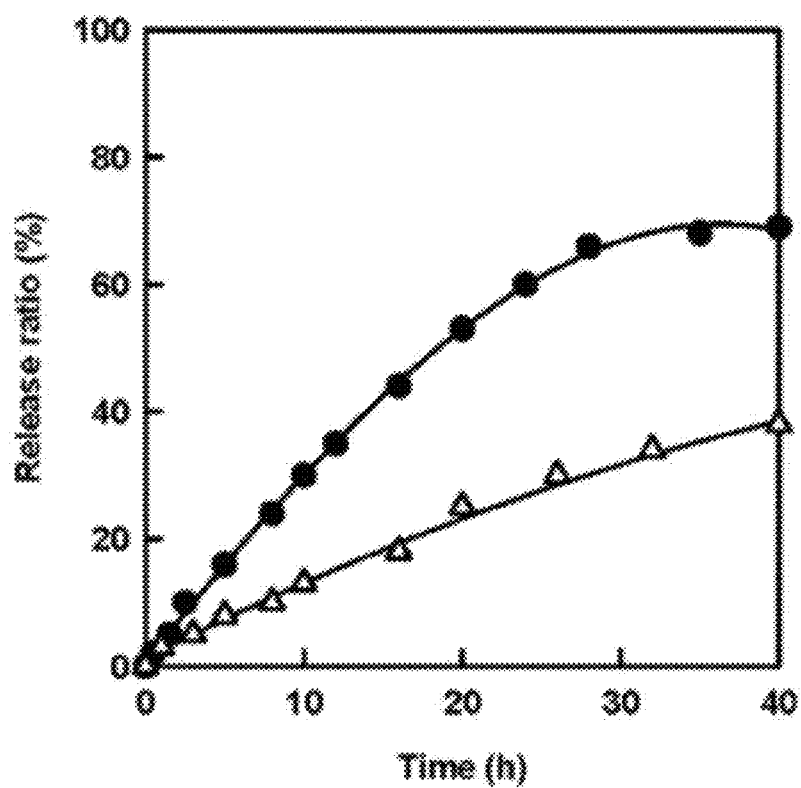

FIG. 12 is a graph showing release of normal GFP from the organic nanotube at pH 8.2. In the graph, ● indicates an organic nanotube having a hydrophobized inner surface formed by Compound-1a of Formula (1) and Compound-2a of Formula (2), and Δ indicates an organic nanotube having a non-hydrophobized inner surface formed by Compound-1a of Formula (1).

Figure 13:
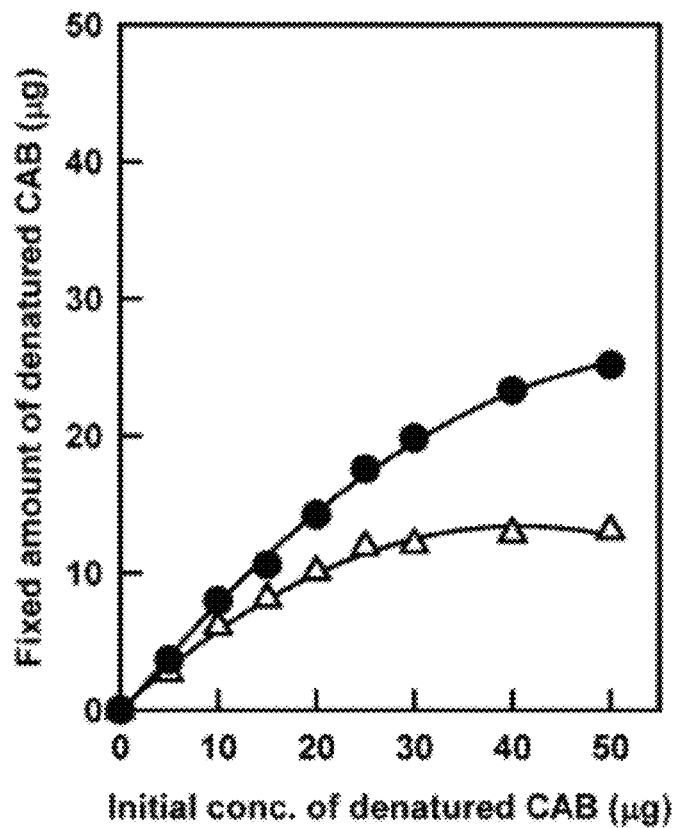

FIG. 13 is a graph showing a relationship between an initial concentration of carbonic anhydrase (CAB) and a concentration of denatured CAB encapsulated in an organic nanotube (5.5 mg). In the graph, ● indicates an organic nanotube having a hydrophobized inner surface formed by Compound-1a of Formula (1) and Compound-2f of Formula (2), and Δ indicates an organic nanotube having a non-hydrophobized inner surface formed by Compound-1a of Formula (1).

Figure 14:
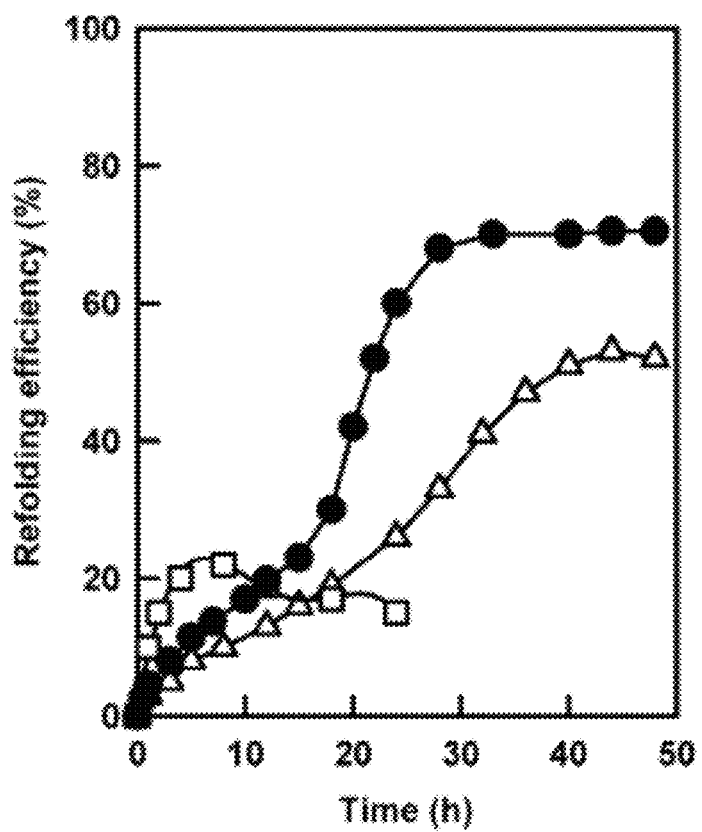

FIG. 14 is a graph showing a recovery rate of normal CAB refolded from denatured CAB. In the graph, ● indicates a recovery rate at pH 7.8 from the organic nanotube having a hydrophobized inner surface formed by Compound-1a of Formula (1) and Compound-2f of Formula (2), Δ indicates a recovery rate at pH 7.8 from the organic nanotube having a non-hydrophobized inner surface formed by Compound-1a of Formula (1), and □ indicates a recovery rate at pH 7 by a dilution method not using the organic nanotube.

Figure 15:
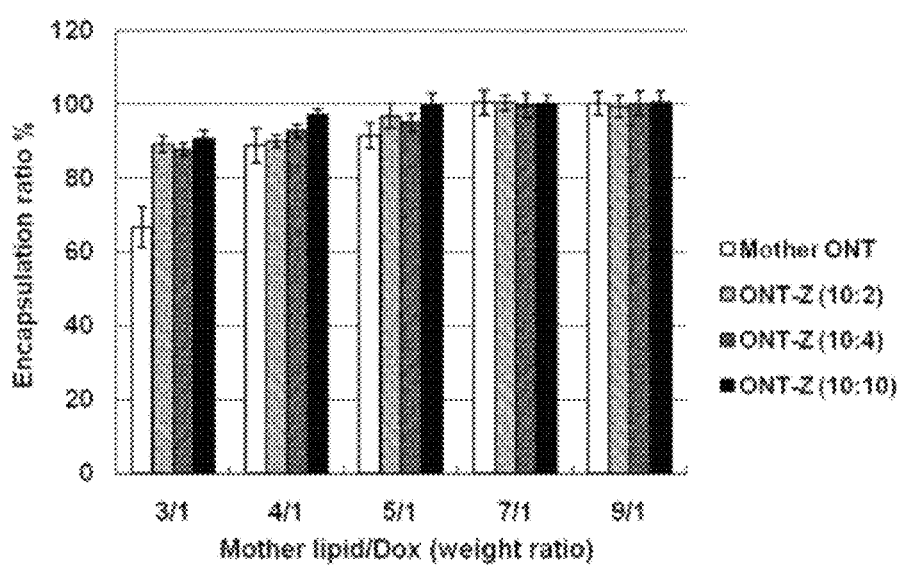

FIG. 15 is a graph showing injection of doxorubicin (at pH 6.5) into the organic nanotube having a hydrophobized inner surface at a various mixing ratio of organic nanotubes to a guest. The horizontal axis indicates the mixing ratio of the organic nanotube having a hydrophobized inner surface and the guest. In the graph, right text indicates compositions of compounds in the organic nanotube. The nanotube made of Compound-1c (G=1-glucopyranosyl group, n=18, $Z_1$=single bond, Y=Gly, m=4, and X=OH) of Formula (1); the nanotube in which a molar ratio of Compound-1c of Formula (1) and Compound-2e of Formula (2) is 10:2; the nanotube in which Compound-1c of Formula (1) and Compound-2e of Formula (2) is 10:4; and the nanotube in which Compound-1c of Formula (1) and Compound-2e of Formula (2) is 10:10, respectively.

Figure 16:
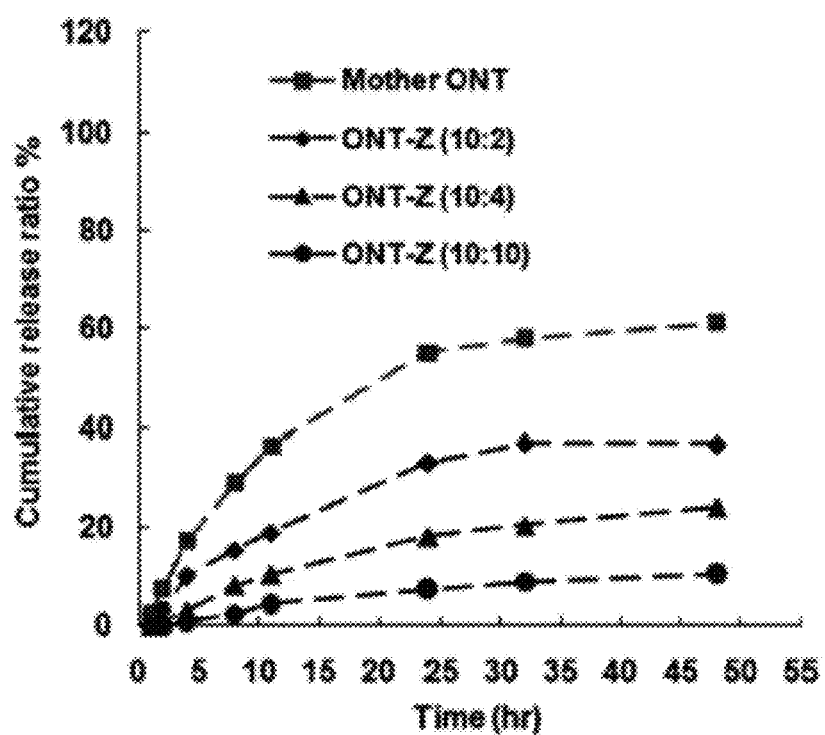

FIG. 16 is a graph showing release of doxorubicin from encapsulated doxorubicin in the organic nanotube having a hydrophobized inner surface (in PBS buffer at pH 7.4). Contents in parenthesis indicate compositions (a mixing ratio of Compound-1c of Formula (1) to Compound-2e of Formula (2)) of the organic nanotube.

Figure 17:
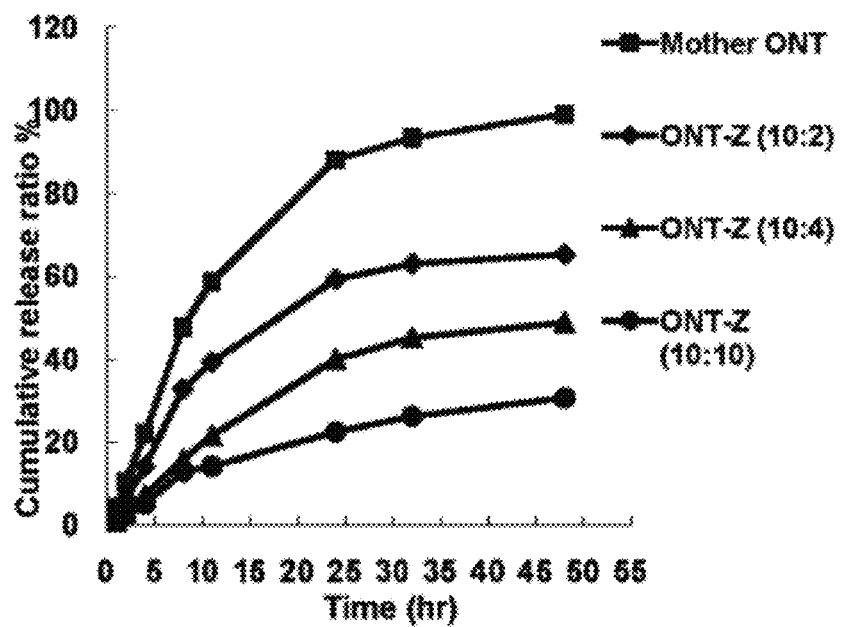

FIG. 17 is a graph showing release of doxorubicin from encapsulated doxorubicin in an organic nanotube having a hydrophobized inner surface (in PBS buffer at pH 5.5). Contents in parenthesis indicate compositions (a mixing ratio of Compound-1c of Formula (1) to Compound-2e of Formula (2)) of the organic nanotube.

Figure 18:
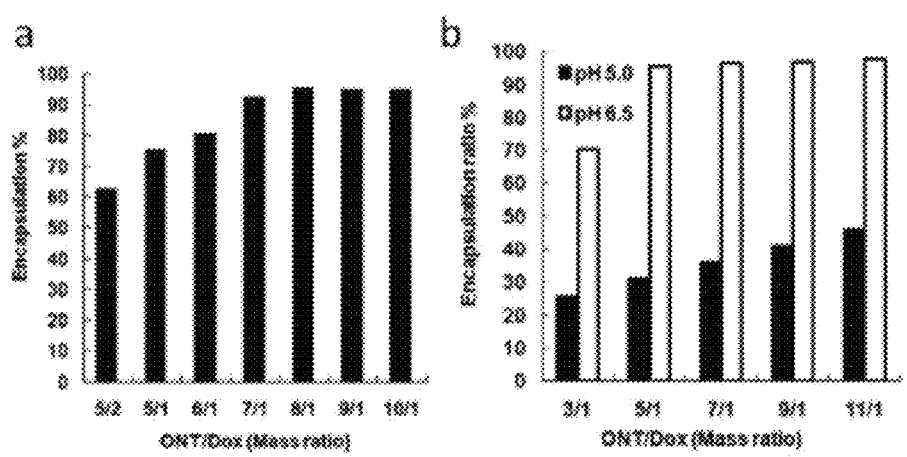

FIG. 18 is graphs showing comparison results of an encapsulation ratio of doxorubicin by the asymmetric nanotube with that in the related art.

(a) The case of "prior application nanotube A".

(b) The case of a symmetric nanotube prepared from Compound-1c of Formula (1) according to the present invention:

In both of (a) and (b), encapsulation was performed in milli Q water, and pH was adjusted using hydrochloric acid, and encapsulation in (a) was performed at pH 6.5 and encapsulation in (b) was performed at pH 5.0 and 6.5. The pH in the graph indicates pH at the time of encapsulation.

Figure 19:
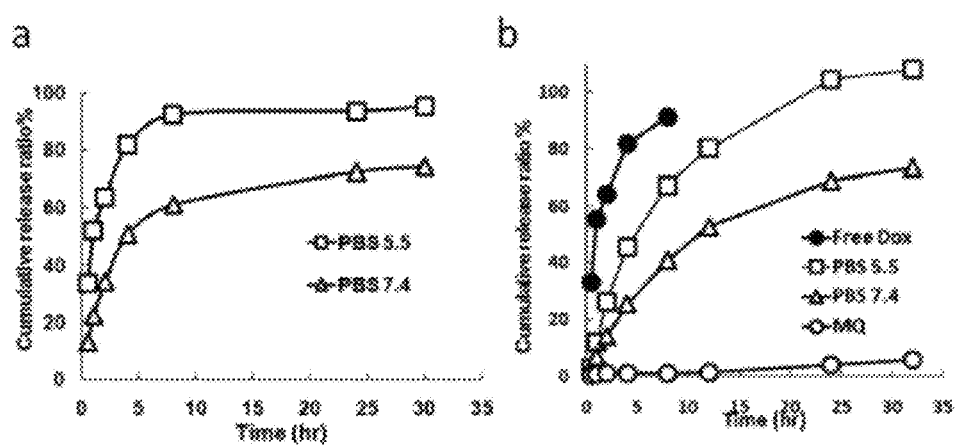

FIG. 19 is graphs showing comparison results of a release property of doxorubicin by the asymmetric nanotube with that in the related art.

(a) In the case of "prior application nanotube A".

(b) The case of a symmetric nanotube prepared from Compound-1c of Formula (1) according to the present invention.

Encapsulation in both of (a) and (b) was performed at a state in which a molar ratio (ONT/DOX) of the nanotube to doxorabicin was 7/1. Numbers in parenthesis in the graph indicate pH of the used PBS buffer.

Figure 20:
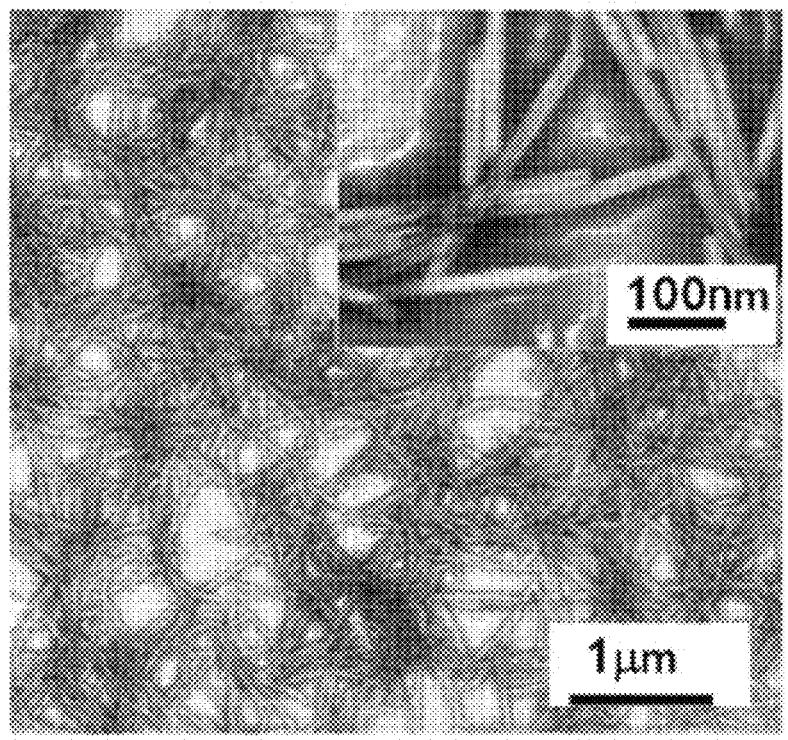

FIG. 20 is a photograph showing evaluation of structural stability of the asymmetric nanotube after 32 hours of doxorubicin release test under physiological conditions (in PBS buffer) in an electron microscopic image (transmission image).

DESCRIPTION OF EMBODIMENTS

1. Organic Nanotube Having a Hydrophobized Inner Surface According to the Present Invention (1-1a) Asymmetric Bipolar Lipid Molecule and Derivatives Thereof Configuring Organic Nanotube Having a Hydrophobized Inner Surface According to the Present Invention The "organic nanotube having a hydrophobized inner surface" according to the present invention is a nanotube formed by binary self-assembly of an asymmetric bipolar lipid molecule represented by General Formula (1) and a derivative thereof represented by General Formula (2), in which a functional group G is localized on an outer surface, and X and R are localized on an inner surface.

[Chemical Formula 1]

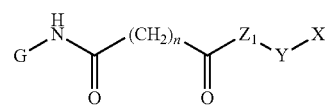

General Formula (1)

[Chemical Formula 2]

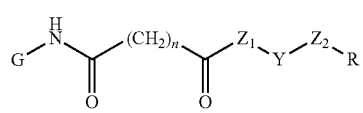

General Formula (2)

In Formulas, G is a 1-glucopyranosyl group or 2-glucopyranosyl group and may exist in a D or L form, but in view of availability, the D form may be preferable. n is any integer of 12 to 22, but in view of availability of a raw material, preferably n is an integer of 12 to 20.

In addition, the same symbols in Formulas (1) and (2) mean the same meaning as each other.

$Z_1$ and $Z_2$ may be a single bond or

[Chemical Formula 3]

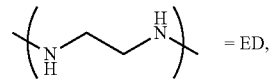

and when $Z_1$ is ED, $Z_2$ may be a single bond.

Y may be

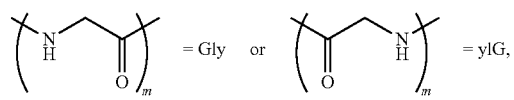

m may be an integer of 2 to 6, and

X is OH when Y is Gly, and X is H when Y is ylG.

R is preferably any one selected from a benzyloxycarbonyl group, a t-butoxycarbonyl group, a 9-fluorenylmethoxycarbonyl group, an acetyl group, an ethylcarbonyl group, a propylcarbonyl group, an alkoxy group having 1 to 4 carbon atoms (preferably, a methoxy group, an ethoxy group, a propyl group, or a t-butoxy group), a benzyloxy group, or a hydrophobic amino acid (preferably, alanine, valine, leucine, isoleucine, methionine, proline, phenylalanine, or tryptophan), and it is preferable that when R is the hydrophobic amino acid, R is bonded to $Z_2$ via an amide bond.

Further, in view of easiness of synthesis, it is preferable that when $Z_1$ is a single bond, Y is Gly, and when $Z_1$ is ED, Y is ylG.

In the "organic nanotube having a hydrophobized inner surface" formed by binary self-assembly of the asymmetric bipolar lipid molecule represented by General Formula (1) and the derivative thereof represented by General Formula (2), including the case of forming a carboxylic acid based asymmetric nanotube having a hydrophobized inner surface to be described below, the asymmetric bipolar lipid molecule and the derivative may be mixed with each other at an arbitrary ratio as long as a nanotubular shape is provided, but in order to control encapsulation or a sustained-release property of a drug or refolding of protein, a component of General Formula (2) is mixed at a ratio of preferably 1 to 60%, and more preferably, 5 to 50%.

(1-1b) Asymmetric Bipolar Lipid Molecule and Derivative Thereof for Configuring Stable Carboxylic Acid Based Asymmetric Nanotube Under Physiological Conditions In the present invention, a stable carboxylic acid based asymmetric nanotube under physiological condition is provided, but the asymmetric bipolar lipid molecule and the derivative thereof for configuring the stable carboxylic acid based asymmetric nanotube are new compounds and are not disclosed in Documents. The asymmetric bipolar lipid molecule can be represented by General Formula (1) or a salt thereof, or an ester derivative thereof, wherein, G is 1-glucopyranosyl or 2-glucopyranosyl, n is an integer of 18 to 22, $Z_1$ is a single bond, Y is Gly, m is an integer of 3 to 6, and X is OH.

Here, the ester derivative corresponds to a compound represented by General Formula (2) where G is 1-glucopyranosyl or 2-glucopyranosyl, n is an integer of 18 to 22, both of $Z_1$ and $Z_2$ are single bonds, Y is Gly, m is an integer of 3 to 6, and R is a methoxy or ethoxy group among alkoxy groups having 1 to 4 carbon atoms, or a benzyloxy group.

The asymmetric bipolar lipid molecules or the esters thereof for forming the carboxylic acid based asymmetric nanotube, which are new compounds of the present invention, have a shape in which a β-D-glucopyranosylamine residue is connected to one end of long-chain carboxylic acid via an amide group, and N-terminal of oligo glycine is condensed at the other end, or the esters thereof. When these lipid molecules or esters thereof are used alone or appropriately mixed with each other, they can form the carboxylic acid based asymmetric nanotube by self-assembly. In this carboxylic acid based asymmetric nanotube, the outer surface is entirely hydrophilic, but since terminal carboxylic groups derived from the original lipid molecules and ester thereof, and/or the ester group are present in the inner surface, the carboxylic acid based asymmetric nanotube may provide a wide inner surface environment ranging from a significantly hydrophobic environment to a significantly hydrophilic environment according to the ratio of each of the functional groups.

Particularly, in the case of mixing the lipid molecule and the ester thereof, the carboxylic acid based asymmetric nanotube having a hydrophobized inner surface may be formed, but m(s) may be different integers of 3 to 6 in Formulas. Representing this case using General Formulas (1) and (2), the carboxylic acid based asymmetric nanotube having a hydrophobized inner surface may be represented by a carboxylic acid based asymmetric nanotube obtained when in General Formulas (1) and (2), wherein n is an integer of 18 to 22, both of $Z_1$ and $Z_2$ are single bonds, m(s) are the same or different integer of 3 to 6, X is OH, and R is a methoxy, ethoxy, or benzyloxy group, but may be represented by the General Formulas (5) and (6).

[Chemical Formula 7]

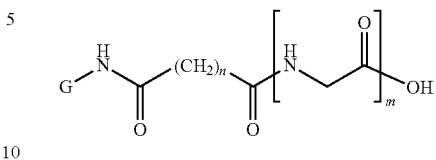

General Formula (5)

(wherein, n is an integer of 18 to 22, and m is an integer of 3 to

[Chemical Formula 8]

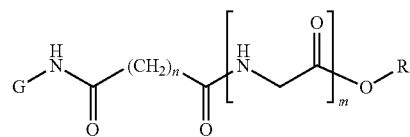

General Formula (6)

(wherein, n has the same meaning as that of General Formula (1), m indicates the same or different integer of 3 to 6, and R indicates a straight chain alkyl group having 1 to 4 carbon atoms).

As described below, both of the compounds of General Formulas (5) and (6) are new, and a new "carboxylic acid based asymmetric nanotube" having an outer surface covered with a 1-glucosamide group and an inner surface covered with a carboxyl group or ester thereof may be formed by individually using this compound or mixing these compounds with each other at an arbitrary ratio. Since a ratio of the carboxylic group or the ester thereof in the inner surface is changed, the compound of General Formula (5) and the compound of General Formula (6) are a combination of the asymmetric bipolar lipid molecule and the ester thereof capable of providing an environment ranging from a significantly hydrophobic environment in which an inner surface of the nanotube is entirely covered with the ester group to a significantly hydrophilic environment in which an inner surface of the nanotube is entirely covered with the carboxylic group, among "organic nanotubes having a hydrophobized inner surface". Generally, the carboxylic acid asymmetric nanotube may be formed by using the preferable mixing ratio for the "organic nanotubes having a hydrophobized inner surface" represented by General Formulas (1) and (2), that is, by mixing a component of General Formula (6) at a ratio of 1 to 60%, preferably, 5 to 50%, based on the content of the component of General Formula (5).

However, since an object of the "carboxylic acid based asymmetric nanotube" is to encapsulate and sustainably release various drugs having various ionic properties and hydrophobicity, it is preferable that the mixing ratio of the lipid molecule and the ester thereof is adjusted according to the properties of a hydrophobic guest to be encapsulated in the nanotube. In detail, in order to encapsulate or sustainably release a cationic drug having significantly high hydrophobicity, it is effective to significantly decrease hydrophilicity of the inner surface. Therefore, it is preferable that the component of General Formula (2) is mixed at a ratio of about 99 to 20%, preferably, 60 to 30%. Meanwhile, in order to encapsulate or sustainably release a cationic drug having high hydrophilicity, it is preferable that a ratio of the carboxyl group is high. Therefore, it is preferable that the component of General Formula (2) is mixed at a ratio of about 50 to 1%, preferably, 30 to 5%.

The asymmetric bipolar lipid molecule according to the present invention may selectively prepare a high purity asymmetric nanotube structure having an outer diameter of about 15 nm and an inner diameter of about 7 to 9 nm by heating and cooling in DMSO and water. To this end, a chain length of an alkylene chain of the lipid molecule according to the present invention should be in a range of 18 to 22, and in view of excellent dispersibility at the time of synthesizing the lipid and easiness of purification, it is more preferable that the alkylene chain has an even chain length. In addition, when the number of oligo glycine residues is 3 or more, particularly 3 to 6, stability of the prepared tube under physiological conditions and preservation stability can be obtained (FIG. 9). Further, the number of oligo glycine residues may be different from each other within this range. The reason is that a multiple cooperative hydrogen bond network referred to as polyglycine II-type between the oligo glycine residues, and the network contributes to stability under physiological conditions or preservation stability. Generally, this hydrogen bond network is seen in a polymer such as polyglycine, but particularly, when the number of glycine residues is 3 or more, an effective network can be formed. Particularly, in the case of the number of glycine residues is 3 or 4, purification at the time of preparing the nanotube is easy in addition to availability of the oligo glycine, so that the object of the present invention can be achieved. In addition, the asymmetric bipolar lipid molecule according to the present invention may be in an aqueous pharmaceutically acceptable salt. For example, a sodium salt thereof, an ammonium salt thereof, or the like, may be preferable.

That is, representing the asymmetric bipolar lipid molecule and the ester thereof according to the present invention using the following General Formula (1),

[Chemical Formula 1]

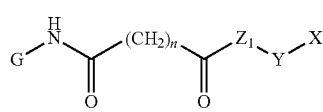

General Formula (1)

[化 2]

[Chemical Formula 2]

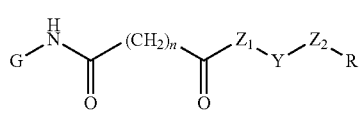

General Formula (2)

the asymmetric bipolar lipid molecule and the ester thereof according to the present invention may be an asymmetric bipolar lipid molecule or an ester derivative thereof represented by General Formulas (1) and (2), wherein G is 1-glucopyranosyl or 2-glucopyranosyl group (however, in view of easiness of synthesis, G is preferably 1-glucopyranosyl group), n is an integer of 18 to 22, $Z_1$ is a single bond, Y is Gly, m is an integer of 3 to 6, and X is OH. $Z_2$ is a single bond, and R is a methoxy or ethoxy group among the alkoxy groups having 1 to 4 carbon atoms, or a benzyloxy group.)

The compound represented by General Formula (1) may be an aqueous pharmaceutically acceptable salt thereof, for example, preferably a sodium salt, a potassium salt, a calcium salt, an ammonium salt.

In addition, in Formulas (1) and (2), wherein n is any integer of 18 to 22, but in view of availability, the raw material, it is preferable that n is 18 to 20. m may be an integer of 3 to 6 or more, but in view of convenience of synthesis, m is preferably 3 to 6. Further, in view of availability in the market, m may be 3 or 4.

In Formula (2), R may be a straight chain alkoxy group having 1 to 4 carbon atoms, a benzyloxy group, or the like, but it is preferable that R is a methyl or ethyl group as a straight chain alkyl group having 1 to 3 carbon atoms.

In addition, the asymmetric bipolar lipid molecule and the ester thereof capable of forming the carboxylic acid based asymmetric nanotube may be represented by the following General Formulas (5) and (6).

[Chemical Formula 7]

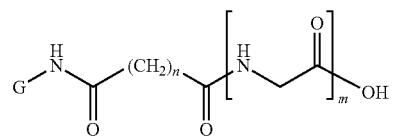

General Formula (5)

(wherein, n is an integer of 18 to 22, and m is an integer of 3 to 6).

[Chemical Formula 8]

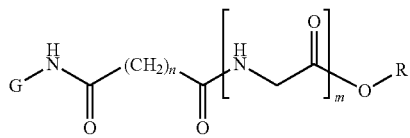

General Formula (6)

(wherein, n has the same meaning as that of General Formula (1), m indicates the same or different integer of 3 to 6, and R indicates a straight chain alkyl group having 1 to 4 carbon atoms).

Unless otherwise defined herein, the same symbols "n, m, R, and the like" used in General Formulas have the same meanings, respectively.

(1-2) Method of Preparing Asymmetric Bipolar Lipid Molecule and Derivative Thereof According to the Present Invention The asymmetric bipolar lipid molecule represented by General Formula (1) and the derivative thereof represented by General Formula (2) may be synthesized via an intermediate (intermediate 3) represented by General Formula (3).

[Chemical Formula 4]

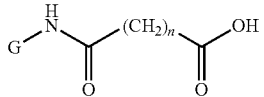

General Formula (3)

In Formula, G is a 1-glucopyranosyl group or 2-glucopyranosyl group and may exist in a D or L form, but in view of availability, the D form may be preferable. Further, for an amino group at 1-position in the case of 1-glucopyranosyl group, α β- or α-amoner or a mixture thereof may be used, but in view of easiness of forming the nanotube, the β-amoner may be suitable. In the case of 2-glucopyranosylamine, a mixture of α- and a β-amoners may be used. A protector (2,3,4,6-tetracetyl-1-glucopyranosyl group) in which the other hydroxyl groups than 1-glucopyranosyl group are acetylated may be used, but finally, deprotection of the acetyl group is required. Deprotection of the acetyl group may be easily performed by using sodium methoxide in methanol (Patent Literature 1 and Non-Patent Literature 8). n is any integer of 12 to 22, but in view of availability of a raw material, preferably, n is 12 to 20.

The compound of General Formula (3) may be synthesized by a condensation reaction of the following 1-glucopyranosylamine, 2,3,4,6-tetracetyl-1-glucopyranosylamine, or 2-glucopyranosylamine and dicarboxylic acid. 1-glucopyranosylamine or 2,3,4,6-tetracetyl-1-glucopyranosylamine may be prepared by methods reported up to now (Non-Patent Literatures 8 and 16, and Patent Literature 1). Dicarboxylic acid may be used in a salt or a monoester (for example, monomethyl ester, monoethyl ester, or benzyl ester) state, but in the case of the monoester, hydrolysis is required after the condensation reaction. The monoester as described above may be synthesized through a hydrolysis reaction after converting dicarboxylic acid into diester with reference to Non-Patent Literature 17. Ester hydrolysis may be performed by alkaline hydrolysis in the case of methyl ester, or the like, and easily performed by catalytic hydrocracking in the presence of palladium carbon in the case of benzyl ester (Patent Literature 1 and Non-Patent Literature 8). Further, in the case of using dicarboxylic acid anhydrate or acid chloride, the active substance needs to be hydrolyzed by adding water after a condensation reaction.

[Chemical Formula 5]

Reaction Formula 1

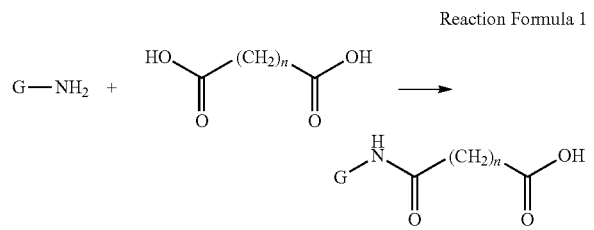

As a condensing agent used in the condensation reaction, various condensing agents used in synthesizing peptides may be used. In detail, "4-(4,6-dimethoxy-1,3,5-triazin-2-yl)-4-methylmorpholinium chloride" (DMT-MM), 1-ethyl-3-(3-dimethylaminopropyl) carbodiimide hydrochloride, dichlorohexylcarbodiimide, diisopropylcarbodiimide, or the like, may be used. Further, although this condensing agent is not used, the corresponding carboxylic acid anhydride or acid chloride may be used. However, DMT-MM capable of providing a condensation product with high yield even in the reaction in water or methanol may be preferable. Further, in the reaction, methanol, ethanol, isopropanol, dimethyl formamide, dimethylacetamide, N-methylpyrrolidone, dimethylsulfoxide, or the like, may be used.

The intermediate (intermediate 3) represented by General Formula (3) may be purified through reprecipitation by heating and cooling using methanol, water containing methanol, or the like, or silica gel column chromatography (developing solvent: for example, chloroform/methanol=20/1).

The derivative represented by General Formula (2) may be synthesized by performing a condensation reaction of the intermediate 3 and a compound of General Formula (4) (Non-Patent Literatures 10 and 18).

[Chemical Formula 6]

General Formula (4)

In Formula
$Z_1$ and $Z_2$ may be a single bond or

[Chemical Formula 3]

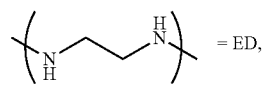

and when $Z_1$ is ED, $Z_2$ may be a single bond.
Y may be

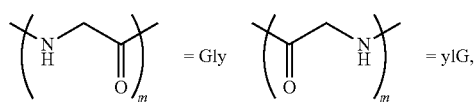

m may be an integer of 2 to 6, and
R is any one selected from a benzyloxycarbonyl group, a t-butoxycarbonyl group, a 9-fluorenylmethoxycarbonyl group, an acetyl group, an ethylcarbonyl group, a propylcarbonyl group, an alkoxy group having 1 to 4 carbon atoms (preferably, a methoxy group, an ethoxy group, or a t-butoxy group), a benzyloxy group, and a hydrophobic amino acid (preferably, alanine, valine, leucine, isoleucine, methionine, proline, phenylalanine, or tryptophan), and when R is hydrophobic amino acid, it is preferable that R is bonded to $Z_2$ via an amide bond.

Further, in view of easiness of synthesis, it is preferable that when $Z_1$ is a single bond, Y is Gly, and when $Z_1$ is ED, Y is ylG.

In General Formula (4), when $Z_1$ and $Z_2$ are single bonds, a commercial product may be used. In the case of other combinations in General Formula (4), the derivative may be synthesized by a condensation reaction of ethylene diamine and oligo glycine of which R is connected to a N-terminal or a condensation reaction of ethylene diamine of which R is connected to other N-terminal and oligo glycine.

The derivative may be synthesized by condensing N-benxyloxy-1,2-diaminoethane with the intermediate 3, performing deprotection, and again performing a condensation reaction with oligo glycine of which R is connected to the N-terminal (Non-Patent Literatures 18 and 19).

As a condensing agent used in the condensation reaction, DMT-MM, 1-ethyl-3-(3-dimethylaminopropyl) carbodiimide hydrochloride, dichlorohexylcarbodiimide, diisopropylcarbodiimide, or the like, may be used. However, DMT-MM capable of providing a condensation product with high yield even in a reaction in water or methanol may be preferable. Further, in the reaction, methanol, ethanol, isopropanol, dimethyl formamide, dimethylacetamide, N-methylpyrrolidone, dimethylsulfoxide, or the like, may be used.

The derivative may be purified through reprecipitation by heating and cooling using methanol, water containing methanol, or the like. The derivative may be identified by element analysis, infrared absorption spectrum, and H-NMR spectrum.

In the derivatives (General Formula (2)) in which $Z_2$ is a single bond and R is a benzyloxycarbonyl group, a t-butoxycarbonyl group, 9-fluorenylmethoxycarbonyl group, a methoxy group, an ethoxy group, t-butoxy group, or a benzyloxy group, since R acts as a protective group of terminal carboxylic acid in the condensation reaction, the asymmetric bipolar lipid molecule represented by General Formula (1) may be synthesized by removing R from the derivatives using a method of removing general protective. The benzyloxycarbonyl group or benzyloxy group may be removed from the derivative by catalytic dehydrogenation reduction using palladium carbon as a catalyst in dimethylformamide (DMF), methanol, methanol/water, or the like. The t-butoxycarbonyl group may be removed from the derivative by acid treatment using hydrochloric acid/organic solvent, trifluoroacetic acid, or the like. The 9-fluorenylmethoxycarbonyl group may be removed from the derivative by base treatment using piperidine, morpholine, diethylamine, or the like. The methoxy, ethoxy, or t-butoxy group may be removed from the derivative by a hydrolysis reaction using acid or alkali in a methanol/water mixed solvent.

Since the removal reaction of R is quantitatively performed, high purity asymmetric bipolar lipid molecules may be obtained, but purification by heating and cooling using methanol, ethanol, DMF, or the like, may be performed, as needed.

In addition, if the compounds of General Formulas (1) and (2) synthesized as described above (General Formulas (5) and (6)), wherein, n is an integer of 18 to 22, both of $Z_1$ and $Z_2$ are single bonds, Y is Gly, m is an integer of 3 to 6, X is OH, and R is a methoxy or ethoxy group among alkoxy groups having 1 to 4 carbon atoms, or benzyloxy group, the compounds are new capable of forming the "carboxylic acid based asymmetric nanotube" according to the present invention.

(1-3) Method of Preparing Organic Nanotube Having Hydrophobized Inner Surface and Carboxylic Acid Based Asymmetric Nanotube In the present invention, since the "carboxylic acid based asymmetric nanotube" among the "organic nanotubes having hydrophobized inner surface" is formed by the new asymmetric bipolar lipid molecule and the ester thereof, the "carboxylic acid based asymmetric nanotube" is new as "the asymmetric nanotube" to thereby be referred to as the "carboxylic acid based asymmetric nanotube". Hereinafter, as needed, separately from the case of a general "organic nanotube having hydrophobized inner surface", the case of a "carboxylic acid based asymmetric nanotube" will be described in detail.

(A) Method of Heating to Dissolving, and Cooling

The case of organic nanotube having hydrophobized inner surface: The asymmetric bipolar lipid molecule (0.5 to 5 mg) represented by General Formula (1) and a derivative thereof of 1 to 60 mol % represented by General Formula (2) are heated at 80 to 100° C. to thereby be completely dissolved in 1 ml of pure water (milli Q water, or the like), followed by cooling (at 0.1 to 10° C./min), thereby making it possible to obtain organic nanotubes having a hydrophobized inner surface. Formation of the organic nanotubes having a hydrophobized inner surface may be confirmed through observation using an electron microscope. A size or hollow cylinder of the organic nanotube having a hydrophobized inner surface of which an outer diameter is about 15 nm, an inner diameter is about 8 to 10 nm, a length is 100 nm to 2 μm may be confirmed by dropping a dispersion solution onto a grid for the electron microscope and staining the inside with an electron beam impermeable stain.

Since the organic nanotube having a hydrophobized inner surface according to the present invention has high structural stability, the organic nanotube can endure physical disturbance such as freeze-drying treatment, sonication. The organic nanotube having a hydrophobized inner surface can be converted into an organic nanotube having a hydrophobized inner surface, having a high yield, a short axial ratio, and high dispersibility by these physical disturbance treatment.

In the case in which solubility of the asymmetric bipolar lipid molecule represented by General Formula (1) or the derivative thereof represented by General Formula (2) for water is low, a dispersion solution of the organic nanotube having a hydrophobized inner surface may be obtained by the same heating and cooling method as described above in dimethylsulfoxide or dimethylformamide. A water dispersion solution can be obtained by suction filtering the dispersion solution and then dispersing the filtrate in water again. As the solvent to be used, in view of solubility, dimethylsulfoxide may be more suitable. In the case of preparing the organic nanotube in dimethylformamide or dimethylsulfoxide, an asymmetric nanotube can be obtained by removing the solvent through concentration under reduced pressure at room temperature, filtration, freeze-drying, and membrane dialysis. In addition, since the solubility is improved, the asymmetric nanotube is suitable for preparation at a concentration of 5 mg/mL or more.

In the case of encapsulating a drug to be administered in a living body, the drug is dissolved or dispersed in water or an aqueous solvent and then used. Therefore, in the case of using water or an aqueous solvent in preparing the asymmetric nanotube, at the time of encapsulating the drug, the asymmetric nanotube can be used as it is in a process of encapsulating the drug without being subjected to a process of removing the solvent.

The case of carboxylic acid based asymmetric nanotube: Among the asymmetric bipolar lipid molecules represented by General Formula (1) and derivatives thereof represented by General Formula (2), in the case of mixing the asymmetric lipid molecule and the ester thereof represented by General Formulas (5) and (6), respectively, an organic nanotube having a hydrophobized inner surface can be formed. However, even in the case of using only a single component to prepare the asymmetric lipid molecule and ester thereof, the asymmetric nanotube can be formed and isolated with the same preparing method. Particularly, in the case in which a length (n) of the hydrophobic alkyl chain is 18 to 22, the solubility at the time of heating is better in dimethylsulfoxide or dimethylformamide used as the solvent. Therefore, the asymmetric nanotube can be prepared at a high concentration. In addition, similarly, when the carboxyl group is changed into salt such as a sodium, potassium, lithium, or ammonium, the solubility at the time of heating in water can be improved, and preparation at a high concentration of 5 mg/mL can be more efficiently performed.

In any of the asymmetric nanotubes, since the outer surface is covered with a 1-glucosamide group, and the inner surface is covered with the carboxyl group or the ester thereof, particularly, both of the nanotubes having the inner surfaces covered with the carboxyl group and the ester thereof, respectively, may be referred to as the "carboxylic acid based asymmetric nanotube". That is, in the case of "carboxylic acid based asymmetric nanotube", even though the nanotube is the organic nanotube having a hydrophobized inner surface, according to the ratio of the carboxylic group or the ester existing in the inner surface, an environment ranging from a significantly hydrophobic environment in which an inner surface of the nanotube is entirely covered with the ester group to a significantly hydrophilic environment in which an inner surface of the nanotube is entirely covered with the carboxylic group can be provided.

The organic nanotube having a hydrophobized inner surface or the carboxylic acid based asymmetric nanotube according to the present invention may encapsulate a cationic material, a material having an amino group, a cationic and hydrophobic material, or the like, (also referred to as a "cationic drug") inside of the tube to slowly release the encapsulated material out of the tube.

(A) Method of Adjusting pH

An asymmetric bipolar lipid molecule represented by General Formula (1) is dispersed and dissolved in about equimolar to 2 molar equivalents of an aqueous sodium hydroxide solution or aqueous hydrochloric acid solution at room temperature, and then a derivative represented by General Formula (2) is added thereto and heated to thereby be dissolved therein. The resultant is cooled to room temperature, and about equimolar to 2 molar equivalents of an acid solution such as hydrochloric acid or an alkaline solution such as sodium hydroxide is added thereto, so that the organic nanotube having a hydrophobized inner surface can be similarly obtained. As the aqueous hydroxide solution, lithium, potassium, rubidium, cesium, and the like, may be used as well as sodium hydroxide, and ammonia may be also used. In addition, as the acid solution, phosphoric acid, formic acid, acetic acid, citric acid, ascorbic acid, sulfuric acid, and the like, may be used as well as hydrochloric acid.

In the case of applying this method of adjusting pH, the organic nanotube can be converted into an organic nanotube having a hydrophobized inner surface having a short axial ratio by sonication, freeze-drying, or the like, and sizes thereof are almost equal to each other. Particularly, in the case of freeze-drying, a concentration of the lipid molecule may be increased to 10 mg/ml in a suitable dispersion state by an amount of water added at the time of rehydration. In addition, the concentration may be increased 10 mg/ml or more (for example, 50 mg/ml), but the nanotube is changed into a gel phase.

(1-4) Stability of Organic Nanotube Having Hydrophobized Inner Surface and Carboxylic Acid Based Asymmetric Nanotube According to the Present Invention The thus-obtained organic nanotube having a hydrophobized inner surface and also the carboxylic acid based asymmetric nanotube can be preserved in the suitable dispersion solution state without occurring precipitation for about 6 months or more even in the case of being preserved at room temperature or cold-preserving at a refrigerator at any concentration. Further, in the case of freeze-drying the dispersion solution, this dispersion solution can be preserved at room temperature for 1 year or more, and the same dispersion solution can be obtained by adding milli Q water, or the like, thereto to perform rehydration.

(1-5) Structures of Organic Nanotube Having Hydrophobized Inner Surface and Carboxylic Acid Based Asymmetric Nanotube According to the Present Invention The tubular structure can be confirmed by visualizing an inner space of the tube through electron microscopic observation after negative staining. That is, a stain not transmitting the electron beam is introduced into an inner space of the tube using a capillary phenomenon to obtain an transmission image by the electron microscopic observation, the inner space of the tube in which the stain is distributed gives a dark image. Since a wall of the tube is made of an organic material through which the electron beam may easily transmit, thin contrast is occurred. The tubular structure may be confirmed by this contrast.

When an inner diameter and a membrane thickness of the obtained nanotube are uniform, and a self-assembly form of the nanotube is not observed, this strongly indicates that two components, that is, the asymmetric bipolar lipid molecule and the derivative thereof, are uniformly mixed with each other.

In the case of the organic nanotube having a hydrophobized inner surface, it can be confirmed by infrared spectrum that the hydrophobic group is localized on the inner surface of the nanotube. The asymmetric bipolar lipid molecules represented by General Formula (1) are packed in parallel with each other by a multipoint hydrogen bond network between molecules referred to as polyglycine II-type at the oligo glycine portions to thereby form a monolayer nanotube. Therefore, the outer and inner surfaces of the nanotube are covered with the glucopyranosyl group and the carboxylic or amino group of the oligo glycine, respectively. When the multipoint hydrogen bond network between molecules is similarly formed between the asymmetric bipolar lipid molecules and the derivative thereof represented by General Formula (2), the carboxyl group or amino group of oligo glycine derived from the asymmetric bipolar lipid molecule and the hydrophobic group derived from the derivative are localized on the inner surface of the nanotube composed of these two components. It will be clearly confirmed by appearance of clear peaks of C—H bending vibration ($1420 \text{ cm}^{-1}$) and backbone vibration ($1026 \text{ cm}^{-1}$) in the infrared spectrum that the polyglycine II-type multipoint hydrogen bond network between molecules is formed (Non-Patent Literature 20). In addition, in a $CH_2$ scissoring vibration absorption peak reflecting a sublattice structure of an oligomethylene chain and a $CH_2$ rocking vibration absorption peak, when a single peak showing triclinic system parallel type is observed at $1465 \text{ cm}^{-1}$ and $719 \text{ cm}^{-1}$, respectively, this result indicates that the asymmetric bipolar lipid molecule and the derivative thereof are aligned in parallel with each other to thereby perform molecular packing.

Further, an asymmetric inner and outer surface structure (that is, a structure oriented so that the carboxylic group or various hydrophobic functional groups are arranged on the inner surface of the tube and the glucopyranosyl group is arranged on the outer surface) may be confirmed from a relationship between a periodic membrane thickness, d of the nanotube obtained from a powder X-ray diffraction pattern of the nanotube and a molecular length L estimated from a molecular model. That is, it is known that in the case in which the asymmetric bipolar lipid molecule forms a nanotube having the asymmetric inner and outer surface structures, the membrane period d of the nanotube and the molecular length L are almost equal to each other or d is slightly smaller than L (L≥d) (Non-Patent Literatures 8 and 19). Therefore, as a result of comparing d and L as described below, since in any cases, the organic nanotube according to the present invention satisfies the above-mentioned relationship (Table 1), it was found that the organic nanotube has the asymmetric inner and outer surface structure.

Table 1 shows the relationship between the membrane periods d of the organic nanotube having a hydrophobized inner surface and the carboxylic acid based asymmetric nanotube obtained by the X-ray diffraction measurement and the molecular length L obtained from the molecular model of the constituent lipid molecules.

In Table 1, as the organic nanotube having a hydrophobized inner surface, the organic nanotube obtained from Compound-1c and Compound-2e (a mixed molar ratio=1/1) in Example 2 was used, and the molecular length L was an average value of those of Compound-1c (4.9 nm) and Compound-2e (5.6 nm). Similarly, d and L of the carboxylic acid based asymmetric nanotube formed in Example 3 based on the asymmetric bipolar lipid molecule (Compound-1c) as the carboxylic acid based asymmetric nanotube, were compared, and the result shows that the above-mentioned relationship (L≥d) was satisfied (Table 1).

Therefore, it was found that all of the organic nanotubes according to the present invention are asymmetric nanotube.

TABLE 1

| Lipid and derivative thereof | Molecular length L (nm) | Membrane period d (nm) |
|---|---|---|
| Nanotube having hydrophobized inner surface | 5.3 (average value) | 3.5 |
| Carboxylic acid based asymmetric nanotube | 4.85 (average value) | 4.3 |

In general, it was known that a series of lipid groups in which only molecular chain lengths are different, in the case in which nanotube structures obtained by self-assembly have almost similar shapes or sizes (inner diameter, outer diameter, wall thickness) to each other, arrangement form of the molecules are similar to each other (Non-Patent Literature 8). Therefore, a long hydrophobic-chain analogues having a length longer than 18 (n=19, 20, 21, or 22) also form the same asymmetric nanotube structure.

2. Function of Refolding Denatured Protein (2-1) Target Denatured Protein

The organic nanotube having a hydrophobized inner surface according to the present invention can stereospecifically refold denatured protein encapsulated in the hollow cylinder so as to have an original stable structure. In detail, as the target denatured protein, there are enzymes (oxidoreductase, transferase, hydrolytic enzymes, lyase, isomerase, or ligase), signal transduction protein, nucleic acid binding protein, receptor protein, energy conversion protein, fluorescent protein, or the like, denatured by guanidine hydrochloride, urea, a surfactant, an organic solvent, a condense salt, pH, or heat. The refolding function may be applied to insoluble protein complex (inclusion body) generated in a mass-production process of recombinant protein using $E.$ $coli$ host, or the like. In this case, it is preferable that the insoluble protein complex is solubilized in advance using guanidine hydrochloride (6 mol/L) or urea (8 mol/L).

(2-2) Method of Encapsulation of Denatured Protein (A) Method of Encapsulation During the Formation of Organic Nanotube Having Hydrophobized Inner Surface An aqueous solution of denatured protein was mixed with an aqueous solution of uniform mixture of the asymmetric bipolar lipid molecule represented by General Formula (1) and the derivative thereof represented by General Formula (2). At this time, it is preferable that the aqueous solution of the lipid molecule of General Formula (1) and the derivative of General Formula (2) is added so that a concentration of a denaturant is diluted to about 1 mol/L. Binary self-assembly is performed by the method of adjusting pH in the presence of the denatured protein, thereby forming an organic nanotube having a hydrophobized inner surface. The denatured protein encapsulated into the organic nanotube having a hydrophobized inner surface is precipitated by centrifugation, and then the non-encapsulated denatured protein contained in supernatant is removed. After adding pure water to perform centrifugation, the denatured protein adsorbed on the outer surface of the organic nanotube having a hydrophobized inner surface is also removed by repeating an operation of removing the supernatant several times. An encapsulation rate may be obtained by calculating a concentration of the recovered non-encapsulated denatured protein using spectroscopic analysis (an ultraviolet absorption method, a bicinchoninic acid method, the Bradford method, the Lowry method, the Biuret method, or the like) and subtracting the calculated concentration from an initial temperature of the denatured protein.

(B) Method of Encapsulation after Forming Organic Nanotube Having Hydrophobized Inner Surface A water dispersion solution (mg/ml order) of the organic nanotube having a hydrophobized inner surface prepared by the method in (1-3) is added to an aqueous solution (mg/ml order) of the denatured protein solubilized by a denaturant such as guanidine hydrochloride (6 mol/L), urea (8 mol/L). In this case, it is preferable that the water dispersion solution of the organic nanotube having a hydrophobized inner surface is added so that a concentration of the denaturant is diluted to about 1 mol/L. Removal of non-encapsulated denatured protein and calculation of a concentration the denatured protein encapsulated in the organic nanotube having a hydrophobized inner surface may be performed similarly to (2-2)(A).

(2-3) Refolding and Release of Denatured Protein

In an aqueous cleaning process for removing the non-encapsulated denatured protein in (2-2), the denaturant is also removed, but it is preferable that a final concentration of the denaturant becomes 0.01 mol/L or less. The refolding of the denatured protein within the hollow cylinder of organic nanotube having a hydrophobized inner surface is performed by re-dispersing the nanotube in an aqueous solution of which pH and a salt concentration are adjusted. It is preferable that the pH is adjusted closely to a neutral range using a phosphate buffer, Good buffers, or the like, but the pH may be adjusted so as to slightly deviate from an isoelectric point of the protein, thereby suppressing association between proteins. In the case of protein having disulfide bonds, since oxidation reduction reactions are carried out, it is necessary to adjust the pH to about 8 (weak alkaline state). As the salt, alkali metal salts or alkali earth metal salts may be preferably used.

The glycine residue derived from the asymmetric bipolar lipid molecule (General Formula (1)) is localized on the inner surface of the corresponding organic nanotube as well as the hydrophobic functional group derived from the derivative (General Formula (2)). Since protons are dissociated from and added to terminal carboxylic groups or amino groups of the glycine residues depending on pH, the inside of the hollow cylinder may become anionic or cationic. Surface charges of the refolded normal protein also become anionic or cationic depending on pH except for at the isoelectric point. In the case in which a charge of the inner surface of the organic nanotube having a hydrophobized inner surface and a surface charge of the normal protein are opposite to each other, an electrostatic interaction occurs therebetween, such that the normal protein is maintained in the hollow cylinder. The normal protein can be released into bulk water by adjusting the pH to reduce or eliminate the electrostatic interaction without adding a special additive.

3. Encapsulation of Hydrophobic Drug and Control of Sustained-Release Thereof (3-1) Target Hydrophobic Protein As a hydrophobic drug capable of being encapsulated in the organic nanotube having a hydrophobic inner surface, there are drugs having a charge opposite to that of the inner surface of the tube and a hydrophobic functional group. The reason is that the drug may be efficiently encapsulated by a hydrophobic interaction between the hydrophobic inner surface of the tube and a hydrophobic portion of the drug in addition to electrostatic attraction between the ionic functional groups of the hydrophobic drug and ionic functional groups of the organic nanotube having a hydrophobized inner surface.

For example, a drug such as doxorubicin, which is an anticancer agent having an amino group, or amiloride (a diuretic), morphine, procaine amide (an antiarrhythmic drug), quinidine (an antiarrhythmic drug), ranitidine (a $H_2$ blocker), tetracycline antibiotics, vancomycin, clarithromycin, or the like, which is a cationic and hydrophobic drug similarly having an amino group, may be encapsulated in an organic nanotube having a hydrophobized inner surface (anionic and hydrophobic nanotube) obtained from a combination of carboxylic acid based lipid molecules of which an inner surface may be negatively ionized among the asymmetric bipolar lipid molecules represented by General Formula (1) and a derivative having a hydrophobic group represented by General Formula (2). In addition, hydrophobicity of the inner surface may be increased by increasing a ratio of a derivative represented by General Formula (2) and having a hydrophobic group at the time of preparing the hydrophobic nanotube. Therefore, encapsulation of a drug having higher hydrophobicity among the cationic drugs or a hydrophobic drug (for example, ibuprofen or vitamin E) may become advantageous. Since the mixing ratio of two components may be set while considering a cationic property and hydrophobicity of the guest to be encapsulated, it is possible to provide an asymmetric nanotube optimal for the guest.

On the contrary, a drug having carboxylic acid such as indomethacin may be encapsulated in an organic nanotube having a hydrophobized inner surface (cationic and hydrophobic nanotube) obtained from a combination of aminebased lipid of which an inner surface may be positively ionized and lipid having a hydrophobic group, or the like.

In addition, since an inner portion of the carboxylic acidbased asymmetric nanotube according to the present invention is covered with the carboxylic group, as a drug preferably encapsulated therein, a compound having a cationic functional group capable of forming an ionic bond with the carboxyl group such as an amino group may be preferable, and a stable cationic drug-asymmetric nanotube complex may be formed. Further, since the tube is filled with negative charges, even though a material is not a compound having a functional group capable of forming a ionic bond, when the material is an entirely cationic with a positive charge and having a size of 0.1 to 5 nm, the material can be encapsulated to form a cationic material-asymmetric nanotube complex.

As a specific example of the cationic drug forming the cationic drug-asymmetric nanotube complex, anthracycline based anticancer agent such as idarubicin, epirubicin, daunorubicin, pirarubicin in addition to doxorubicin, or other drugs having an amino group or pyridine group may be preferably used. In addition, drugs such as cisplatin, nedaplatin, carboplatin, oxliplatin may be preferable in that they interact with the carboxyl group of the inner surface of the tube.

As the matter of course, the asymmetric nanotube according to the present invention may be applied to various additives such as a cationic emulsifier for cosmetic or food, a dispersant, a stabilizer, a moisturizer as well as drugs having a pharmacological action as a medicinal drug.

(3-2) Method of Encapsulation of Hydrophobic Drug

In the case of a drug soluble in water among the hydrophobic drugs, encapsulation may be achieved by dispersing the organic nanotube having a hydrophobized inner surface in water and adding the hydrophobic drug, followed by stirring. For example, a solution in which a cationic material to be encapsulated is dissolved or suspended in pure water (milli Q water) so as to have a concentration of 0.1 to 50 mg/mL and a dispersion solution (concentration: 0.1 to 20 mg/mL) of the asymmetric nanotube according to the present invention are equivalently mixed with each other and left at room temperature for 10 minutes to 24 hours. In this case, an encapsulation ratio of 30 to 95% may be achieved. Therefore, for example, in the case of using this nanotube as a composition for an anticancer agent, or the like, the entire amount of the composition for allowing an effective amount to be contained may be decreased.

In the case of a drug insoluble in water among the hydrophobic drugs, it is necessary to use an (mixed or pure) organic solvent not destroying a tube structure while allowing the drug to be encapsulated to be soluble such as DMSO, DMF, alcohol. In addition, since solubility of the nanotube may be changed according to the temperature, it is important to select a temperature at which the nanotube is not destroyed. After mixing the drug and the nanotube in a state in which the drug may be dissolved and a shape of the nanotube may be maintained, the mixture is left for 10 minutes to about 24 hours, so that encapsulation can be achieved.

A material that is not encapsulated may be efficiently removed by filtering the mixed solution using a porous membrane (200 nm). Since only the tube encapsulating the cationic material can be isolated as a solid by the above-mentioned method, a concentration of the tube containing the encapsulated cationic material may be adjusted by re-dispersing the tube encapsulating cationic material in milli Q water at an arbitrary concentration. In addition, similarly, the concentration of freeze-dried solid of the tube encapsulating the cationic material may also be adjusted by dispersing a solid into milli Q water at an arbitrary concentration.

The encapsulation ratio of the drug may be quantified by measuring unique UV absorption of the drug in a solution, obtained by filtering and isolating the nanotube after encapsulating the drug as described above and then re-dispersing the isolated nanotube in milli Q water. For example, in the case of doxorubicin, 200 μL of doxorubicin solution (arbitrary amounts of doxorubicin (2.0 to 0.5 mg/per 1 mL) dissolved in milli Q water, respectively) and 200 μL of the nanotube dispersion solution (5 mg/mL) were mixed, and then left at room temperature for 30 minutes. Two handred micro litter of the resultant was extracted, filtered through a porous membrane (200 nm), and then washed with 400 μL of milli Q water. The filtered and isolated solid (nanotube) on each filter paper was re-dispersed in 200 μL of milli Q water. UV absorption at 480 nm of doxorubicin of the solution before and after filtering were compared with each other, thereby obtaining the encapsulation ratio.

In the case of encapsulation in an aqueous solution using an anionic and hydrophobic nanotube, as a ratio of the derivative represented by General Formula (2) and having a hydrophobic portion is increased, the encapsulation ratio of a drug is improved. Particularly, it was found that in the case in which an amount of drug to be encapsulated in the nanotube is large, the encapsulation ratio may be increased by about 10% by adding the hydrophobic portion as compared to the carboxylic acid based asymmetric nanotube.

(3-3) Control of Sustainably Release of Hydrophobic Drug

The hydrophobic drug may be sustainably released from the nanotube having a hydrophobized inner surface in various solvents such as water based solvents, organic solvents. In order to maintain electrostatic attraction between the nanotube and the drug and sustained-release the drug for a longer time, it is preferable that a salt concentration of a medium is suppressed as much as possible. The sustained release property of the encapsulated drug may be controlled by changing a mixing ratio of the asymmetric bipolar lipid molecule and the derivative thereof.

In addition, in both of the organic nanotube having a hydrophobized inner surface having a carboxyl group on the inner surface and the carboxylic acid based asymmetric nanotube, the drug may be condition-selectively and efficiently released by a change in an ionization state of the carboxyl group localized on the inner surface of the tube according to the external stimulus such as a change in pH. Particularly, since the carboxyl group on the inner surface is protonated by adding a buffer solution in the nanotube dispersion solution of milli Q water to adjust the pH to 4 to 6, release of the drug may be accelerated. Further, the drug may be sustainably released by adjusting the pH to 7 to 8.

In addition, it may be expected that an amount of drug delivered to the target cancer cells or tissue is increased due to an enhanced permeability and retention (EPR) effect by using a nanotube of which a size is decreased to about 50 to 500 nm by sonication, or the like, as the organic nanotube having a hydrophobized inner surface and the carboxylic acid based asymmetric nanotube according to the present invention.

A release amount of drug from the nanotube may be quantitatively measured by sealing the tube dispersion solution in an inner aqueous phase of a dialysis membrane tube (molecular weight cut-off: about 1200 to 20000) and measuring an amount of the drug passing through the membrane to thereby be released to an outer aqueous phase using UV spectroscopy, or the like.

For example, in the case of an asymmetric nanotube encapsulating doxorubicin (nanotube/doxorubicin=8/1) in a PBS buffer (pH 7.4), this nanotube was sealed in a dialysis membrane (molecular weight cut-off: 14000), and the dialysis membrane tube was put into an outer aqueous phase in the same PBS buffer (pH 7.4). Then, a release amount of doxorubicin in an outer aqueous phase was monitored by UV absorption while stirring.

4. Encapsulated Drug Composition (4-1) Drug Composition

Since the organic nanotube having a hydrophobized inner surface and the carboxylic acid based asymmetric nanotube according to the present invention have excellent properties as a drug carrier, an asymmetric nanotube complex containing an effective amount of therapeutic drug may be used in a drug composition as an active component together with a pharmaceutically acceptable carrier. In addition, the drug composition may include medicinal compositions for preventing, curing, or treating cancer, for example, anticancer agents. Further, since the drug composition is effective in the case of allowing the drug to be slowly released in an aqueous environment, a cationic drug composition blended as cosmetics or food may also be included in the drug composition.

As a typical example of the encapsulated drug of the present invention, there are anthracycline based anticancer agents such as the above-mentioned doxorubicin, idarubicin, epirubicin, daunorubicin, pirarubicin, or other drugs having an amino group. In addition, cationic drugs such as cisplatin, nedaplatin, carboplatin, oxliplatin may be similarly used. Further, in the case in which the inner surface of the asymmetric nanotube is covered with a carboxylic acid ester group, a mixture of a carboxyl acid group and an ester thereof, or a mixture of the carboxylic acid group and a hydrophobic amide group, and in the case of the drug composition in which a drug having higher hydrophobicity among the cationic drugs or a hydrophobic drug (for example, ibuprofen or vitamin E) is encapsulated, the drug composition may be more effective.

Here, the pharmaceutically acceptable carrier includes a diluent or an excipient, for example, water or a physiologically acceptable buffer solution.

The drug composition according to the present invention may be orally administered such as tablets, but also be parenterally administered, for example, intravenous injected, directly injected to the affected part, externally applied.

A dose at the time of administering the drug composition according to the present invention to a patient may be suitably determined depending on a kind of used drug, an age and a weight of a target patient, symptoms of disease, an administration route, or the like, but typically, an effective single dose of the drug may be in a range of 1 µg to 1 g, preferably 100 µg to 10 mg.

(4-2) Functions of Drug Composition

In the encapsulated medicinal agent by the organic nanotube having a hydrophobized inner surface and the carboxylic acid based asymmetric nanotube according to the present invention, three effects can be expected, that is, a sustained-release action capable of slowly releasing the medicinal agent at near neutral pH, accelerated release effect under an acidic condition, and a control of sustained-release by controlling hydrophobicity of the inner surface of the tube in the case of the organic tube having a hydrophobized inner surface. That is, in the case of cancer cells, three effects can be expected, that is, an effect of selectively releasing a drug in the vicinity of cancer tissue that is in a slightly acidic state, an effect of expressing high anticancer activity by rapidly releasing the drug in cancer cells, an effect of improving a medicinal effect while further suppressing side effects derived from toxicity by controlling a sustained-release rate.

In addition, as used herein, the term "cell" typically indicates a mammal cell including a human cell. These cells may be cells cultured in vitro, but in the case of drug therapy, tissue configuring a living body, cells in an organ, blood cells in body fluids such as blood, immune cells such as lymphocyte cells, various cancer cells may become a target.

(4-3) Cytotoxicity Evaluation of Drug Composition In Vitro

Toxicity evaluation may be performed by adding and culturing encapsulated doxorubicin in various asymmetric nanotubes using HeLa cells and evaluating the number of cells. Comparison with doxorubicin itself and evaluation of nanotube itself may be performed by the same method.

EXAMPLES

Next, the present invention will be described in more detail with reference to Examples, but the present invention is not limited thereto.

Other terms or concepts in the present invention is based on meanings conventionally used in the art, and various techniques used to practice the present invention except for techniques of which sources are indicated are based on the known literatures and easily and surely implemented by those skilled in the art. In addition, various analyses, or the like were performed by the method disclosed in instruction manuals, catalogs, or the like of used analysis equipments, reagents, or kits.

Further, technical documents, patent publications, and patent application specification cited herein will be referred to as the description of the present invention.

Reference Example 1

Preparation of 1-β-D-Glucopyranosylamine

D-glucose (1.8 g, 10 mmol), ammonium bicarbonate (0.8 g, 10 mmol), and 28% aqueous ammonia (55 ml) were put in a branched flask and stirred at 41° C. for 48 hours. The reaction solution was condensed under reduced pressure and freeze-dried, thereby obtaining the desired 1-β-D-glucopyranosylamine as a solid.

Reference Example 2

Preparation of Intermediate 3 Represented by General Formula (3) (G is a 1-β-D-Glucopyranosyl Group, and n=18)

746 mg of eicosane diacid monomethyl ester (2.1 mmol) was dissolved in 33 ml of methanol and 17 ml of ethyl acetate, and then 405 mg of DMT-MM (1.47 mmol) and 250 mg of 1-β-D-glucopyranosylamine (1.4 mmol) were added thereto, followed by stirring at room temperature for 4.5 hours. The reaction solution was filtered, thereby obtaining methyl ester of the desired Intermediate 3 as a white solid. Methyl ester (257 mg, 0.5 mmol) of the desired Intermediate 3 was dispersed in a methanol/water solvent, and then 0.9 ml of an aqueous sodium hydroxide solution (1 mol/L) was added thereto to perform hydrolysis at 60° C. After adjusting a pH to 4 by adding hydrochloric acid, insoluble white solid was filtered, thereby obtaining 171 mg of the desired intermediate 3 (24%) as a white solid.

Preparation Example 1

Synthesis of Asymmetric Bipolar Lipid Molecule (Compound-1a of Formula (1), G=1-β-D-Glucopyranosyl Group, n=16, $Z_1$=ED, Y=ylG, m=3, and X=H)

Lipid molecules (Compound-1a) among the asymmetric bipolar lipid molecules represented by General formula (1) wherein G was a 1-β-D-glucopyranosyl group, n was 16, $Z_1$ was ED, Y was ylG, m was 3, and X was H) were synthesized according to the method disclosed in Non-Patent Literature 18. Compound-1a was confirmed through $^1$H-NMR, IR, and element analysis.

Preparation Example 2

Synthesis of Asymmetric Bipolar Lipid Molecule (Compound-1b of Formula (1), G=1-β-D-Glucopyranosyl Group, n=18, $Z_1$-ED, Y=ylG, m=3, and X=H)

Lipid molecules (Compound-1b) among the asymmetric bipolar lipid molecules represented by General Formula (1) wherein G was a 1-β-D-glucopyranosyl group, n was 18, $Z_1$ was ED, Y was ylG, m was 3, and X was H were synthesized by the method in Example 1 using eicosane diacid as a raw material. Compound-1b was confirmed through $^1$H-NMR and IR.

$^1$H-NMR (DMSO-$d_6$ with a drop of $D_2O$, 400 MHz) 1.23 (s, 28H, —$CH_2$—), 0.47 (m, 4H, —$CH_2$—), 2.07 (m, 4H, —$CH_2C$=O), 3.08 (m, 3H, H-2, H-4, H-5), 3.09 (m, 4H, NH—$CH_2C$=O), 3.18 (t, 1H, H-3), 3.62 (m, 4H, —NH—C $H_2$—, —$CH_2$—$NH_2$), 3.68 (d, 2H, H-6a, H-6b), 3.85 (s, 2H, —NH—$CH_2$—), 4.68 (t, 1H, H-1), 7.95 (m, 2H, NH), 8.32 (m, 2H, NH)

Preparation Example 3

Synthesis of Derivative (Compound-2a of Formula (2), G=1-β-D-Glucopyranosyl Group, n=16, $Z_1$=ED, Y=ylG, m=3, $Z_2$=Single Bond, and R=Benzyloxycarbonyl Group)

Since a derivative (Compound-2a) among those represented by General Formula (2) wherein G was a 1-β-D-glucopyranosyl group, n was 16, $Z_1$ was ED, Y was ylG, m was 3, $Z_2$ was a single bond, and R was a benzyloxycarbonyl group was a precursor of Compound-1a, the derivative was obtained during a synthesis process of Compound-1a. Compound-2a was confirmed through $^1$H-NMR.

$^1$H-NMR (DMSO-$d_6$ with a drop of $D_2O$, 400 MHz) 1.24 (s, 24H, —$CH_2$—), 1.47 (m, 4H, —$CH_2$—), 2.04 (m, 4H, —$CH_2C$=O), 3.05 (m, 3H, H-2, H-3, H-5), 3.08 (m, 4H, N—$CH_2$—$CH_2$—N), 3.16 (m, 1H, H-4), 3.40 (m, 2H, H-6), 3.63 (m, 2H, H-6), 3.65 (d, 2H, N—$CH_2C$=O), 3.67 (d, 2H, N—$CH_2C$=O), 3.75 (d, 2H, N—$CH_2C$=O), 4.69 (t, 1H, H-1), 5.03 (s, 2H, —$CH_2$-Phe), 7.35 (m, 5H, Phe), 7.50 (t, 1H, NH), 7.81 (d, 2H, NH), 8.12 (t, 1H, NH), 8.16 (t, 1H, NH), 8.61 (d, 1H, NH)

Preparation Example 4

Synthesis of Derivative (Compound-2c of Formula (2), G=1-β-D-Glucopyranosyl Group, n=18, $Z_1$=Single Bond, Y=Gly, m=4, $Z_2$=Single Bond, and R=Methoxy Group)

Figure 1:
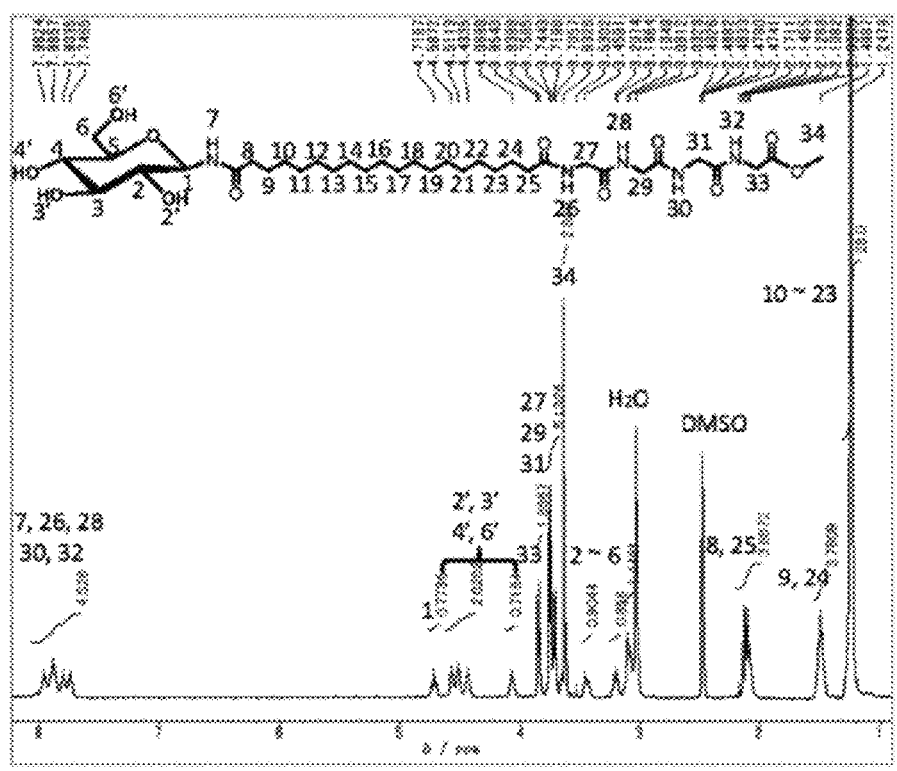
FIG. 1 is a graph showing a $^1$H-NMR spectrum (dimethyl sulfoxide (DMSO)-$d_6$ with a drop of $D_2O$, 60° C.) of Compound-2c (in Formula (2), G=1-glucopyranosyl group, n=18, $Z_1$=single bond, Y=Gly, m=4, $Z_2$=single bond, and X=methoxy group).

A derivative (Compound-2c) among those represented by General Formula (2) wherein G was a 1-β-D-glucopyranosyl group, $Z_1$ was a single bond, Y was Gly, m was 4, $Z_2$ was a single bond, and R was a methoxy group was synthesized by using Intermediate 3 obtained by the method in Patent Literature 1 or Non-Patent Literature 8 as a raw material, adding 115 mg of tetra glycine methyl ester (0.44 mmol) and DMT-MM to 200 mg of Intermediate 3 (0.4 mmol) in 20 ml of DMF, and then stirring them at room temperature for 2 hours. The reaction solution was condensed under reduced pressure, followed by reprecipitation in methanol and suction-filtration, thereby obtaining Compound-2c as a white solid. Compound-2c was confirmed through $^1$H-NMR (FIG. 1).

$^1$H-NMR (DMSO-$d_6$ with a drop of $D_2O$, 400 MHz) 1.23 (s, 28H, —$CH_2$—), 1.47 (m, 4H, —$CH_2$—), 2.07 (m, 4H, —$CH_2C$=O), 3.08 (m, 3H, H-2, H-4, H-5), 3.09 (m, 4H, NH—$CH_2C$=O), 3.18 (t, 1H, H-3), 3.62 (m, 4H, —$NH_1$—$CH_2$—, —$CH_2$—$NH_2$), 3.68 (d, 2H, H-6a, H-6b), 3.85 (s, 2H, —NH—$CH_2$—), 4.68 (t, 1H, H-1), 7.95 (m, 2H, NH), 8.32 (m, 2H, NH).

Preparation Example 5

Synthesis of Asymmetric Bipolar Lipid Molecule (Compound-1c of Formula (1), G=1-β-D-Glucopyranosyl Group, n=18, $Z_1$=Single Bond, Y=Gly, m=4, and X=OH)

Figure 2:
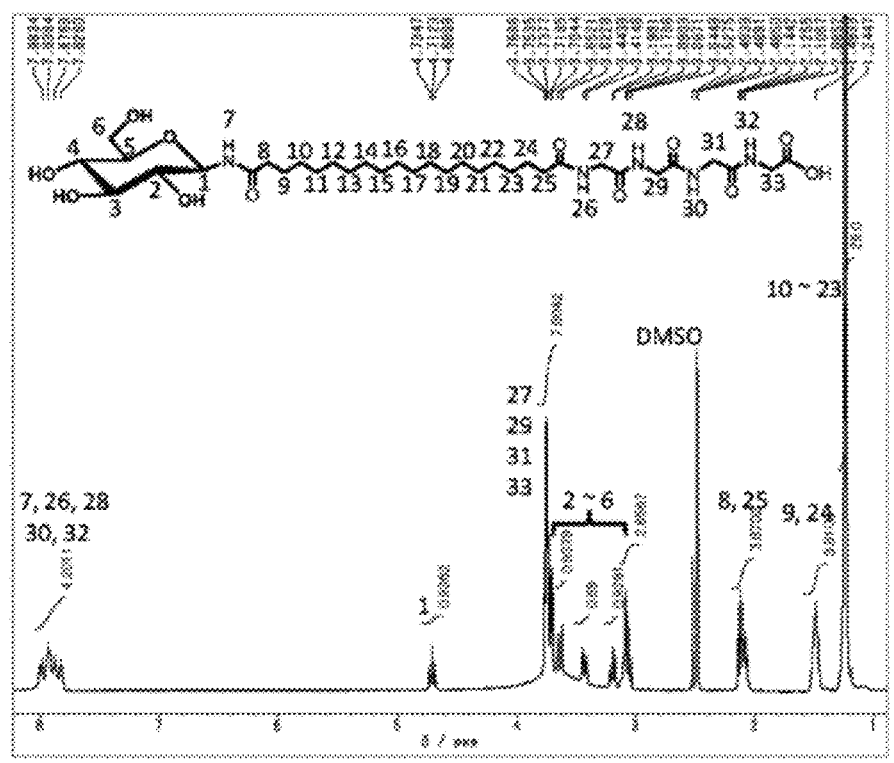
FIG. 2 is a graph showing a $^1$H-NMR spectrum (DMSO-$d_6$ with a drop of $D_2O$, 60° C.) of Compound-1c (in Formula (1), G=1-glucopyranosyl group, n=18, $Z_1$=single bond, Y=Gly, m=4, and X=OH).

Lipid molecules (Compound-1c) among the asymmetric bipolar lipid molecules represented by General Formula (1) wherein G was a 1-β-D-glucopyranosyl group, n was 18, $Z_1$ was a single bond, Y was Gly, m was 4, and X was OH were prepared from the derivative (Compound-2c of Formula (2)) obtained in Preparation Example 4. Two hundred fifty milligram of the derivate (Compound-2c of General Formula (2), 0.34 mmol) was dissolved in 25 ml of ethanol/water (1:1 volume ratio), and 0.38 ml of 1N aqueous NaOH was added thereto. After the mixed solution was stirred at 90° C. for 10 minutes to perform hydrolysis, 0.4 ml of 1N aqueous HCl solution was added to neutralize the mixed solution so as to make pH to become about 4, and then the precipitated solid was filtered and dried, thereby obtaining 215 mg of Compound-1c (yield: 85%). Compound-1c was confirmed through $^1$H-NMR (FIG. 2).

$^1$H-NMR (DMSO-$d_6$ with a drop of $D_2O$, 400 MHz) 1.23 (s, 28H, —$CH_2$—), 1.47 (m, 4H, —$CH_2$—), 2.07 (m, 4H, —$CH_2C$=O), 3.08 (m, 3H, H-2, H-4, H-5), 3.09 (m, 4H, $NH_1$—$CH_2C$=O), 3.18 (t, 1H, H-3), 3.62 (m, 4H, —NH—$CH_2$—, —$CH_2$—$NH_2$), 3.68 (d, 2H, H-6a, H-6b), 3.85 (s, 2H, —NH—$CH_2$—), 4.68 (t, H, H-1), 7.95 (m, 2H, NH), 8.32 (m, 2H, NH)

Preparation Example 6

Synthesis of Derivative (Compound-2d of Formula (2), G=1-β-D-Glucopyranosyl Group, n=18, $Z_1$=Single Bond, Y=Gly, m=4, $Z_2$=Single Bond, and R=Benzyloxy Group)

Figure 3:
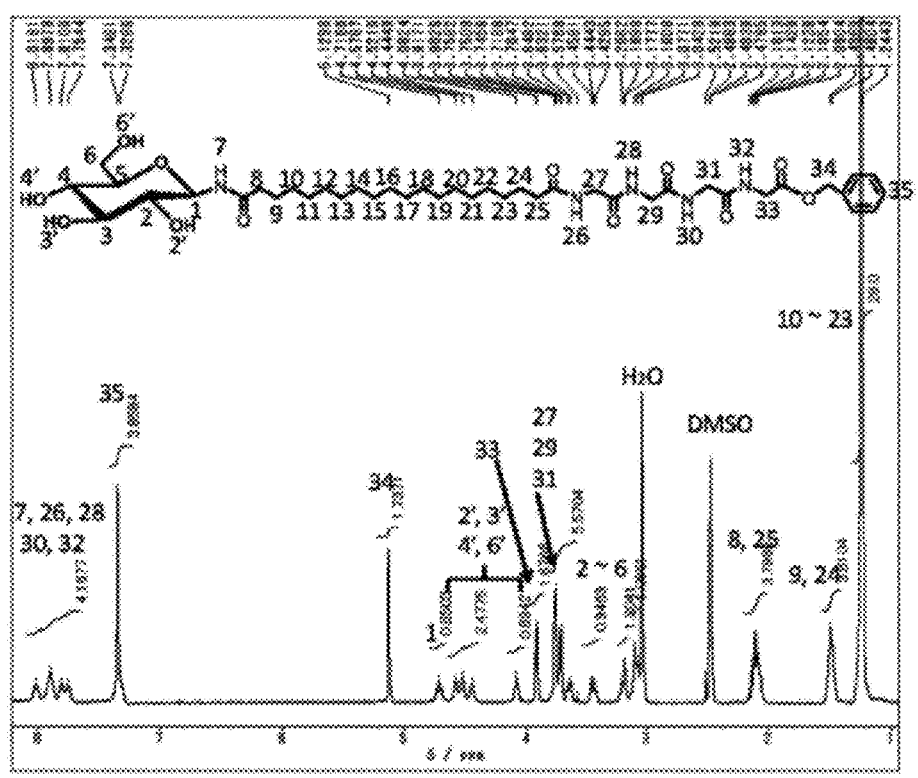
FIG. 3 is a graph showing a $^1$H-NMR spectrum (DMSO-$d_6$ with a drop of $D_2O$, 60° C.) of Compound 2d (in Formula (2), G=1-glucopyranosyl group, n=18, $Z_1$=single bond, Y=Gly, m=4, $Z_2$=single bond, and R=benzyloxy group).

A derivative represented by General Formula (2) wherein G was a 1-β-D-glucopyranosyl group, $Z_1$ was a single bond, Y was Gly, m was 4, $Z_2$ was a single bond, and R was a benzyloxy group was synthesized by using Intermediate-3 obtained by the method described in Preparation Example 4 as a raw material, adding 80 mg of tetra glycine benzyl ester (0.24 mmol) and DMT-MM to 100 mg of Intermediate-3 (0.2 mmol) in 10 ml of DMF and then stirring them at room temperature for 2 hours. The reaction solution was condensed under reduced pressure, followed by reprecipitation in methanol and suction-filtration, thereby obtaining 150 mg of Compound-2d (0.18 mmol, yield: 90%) as a white solid. Compound-2d was confirmed through $^1$H-NMR t (FIG. 3).

$^1$H-NMR (DMSO-$d_6$ with a drop of $D_2O$, 400 MHz) 1.23 (s, 28H, —$CH_2$—), 1.47 (m, 4H, —$CH_2$—), 2.07 (m, 4H, —$CH_2C$=O), 3.08 (m, 3H, H-2, H-4, H-5), 3.09 (m, 4H, NH—$CH_2C$—O), 3.18 (t, 1H, H-3), 3.62 (m, 4H, —NH—$CH_2$—, —$CH_2$—$NH_2$), 3.68 (d, 2H, H-6a, H-6b), 3.85 (s, 2H, —NH—$CH_2$—), 4.68 (t, 1H, H-1), 7.95 (m, 2H, NH), 8.32 (m, 2H, NH).

Preparation Example 7

Synthesis of Derivative (Compound-2e of Formula (2), G=1-β-D-Glucopyranosyl Group, n=18, $Z_1$=Single Bond, Y=Gly, m=3, $Z_2$=ED, and R=Benzyloxycarbonyl Group)

Figure 4:
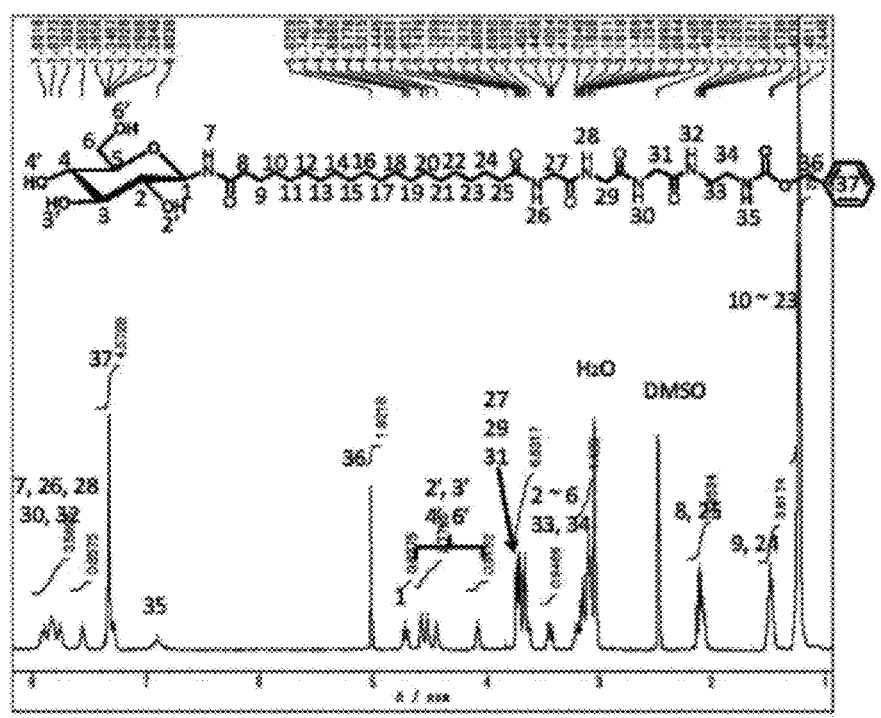
FIG. 4 is a graph showing a $^1$H-NMR spectrum (DMSO-$d_6$ with a drop of $D_2O$, 60° C.) of Compound 2e (in Formula (2), G=1-glucopyranosyl group, n=18, $Z_1$=single bond, Y=Gly, m=3, $Z_2$=ED, and R=benzyloxycarbonyl group).

Synthesis of a compound of General Formula (4) ($Z_1$ was a single bond, Y was Gly, m was 3, $Z_2$ was ED, and R was a benzyloxycarbonyl group) which became a portion of the derivative (Compound-2e of Formula (2)) among the derivatives represented by General Formula (2) wherein G was a 1-β-D-glucopyranosyl group, n was 18, $Z_1$ was single bond, Y was Gly, m was 3, $Z_2$ was ED, and R was benzyloxycarbonyl group was conducted. Boc-N-triglycine (2 g, 6.9 mmol) was dissolved in 50 ml of anhydrous methanol, and 1.7 g of mono N-benzyloxycarbonylethylenediamine hydrochloride (7.2 mmol), 1.1 ml of triethylamine, and DMT-MM were added thereto, followed by stirring at room temperature for 3 hours. After the reaction solution was condensed (to 20 ml) under reduced pressure, the resultant was added to 20 ml of 4N hydrochloric acid-ethyl acetate solution at 4° C. and stirred the mixture, thereby obtaining 2.4 g of hydrochloride salt (87%) of the compound of General Formula (4) ($Z_1$ was a single bond, Y was Gly, m was 3, $Z_2$ was ED, and R was a benzyloxycarbonyl group) as a precipitate. Intermediate-3 obtained by the method described in the above-mentioned Preparation Example 4 was used as a raw material. Using 200 mg of Intermediate-3 (0.4 mmol) as a raw material, 175 mg of the compound (0.44 mmol) of General Formula (4) ($Z_1$ was a single bond, Y was Gly, m was 3, $Z_2$ was ED, and R was a benzyloxycarbonyl group), DMT-MM, and triethylamine were added and stirred at room temperature for 2 hours. The reaction solution was condensed under reduced pressure, followed by reprecipitation in methanol and suction-filtration, thereby obtaining 310 mg of Compound-2e (0.36 mmol, yield: 90%) as a white solid. Compound-2e was confirmed through $^1$H-NMR (FIG. 4).

$^1$H-NMR (DMSO-$d_6$ with a drop of $D_2O$, 400 MHz) 1.23 (s, 28H, —$CH_2$—), 1.47 (m, 4H, —$CH_2$—), 2.07 (m, 4H, —$CH_2C$=O), 3.08 (m, 3H, H-2, H-4, H-5), 3.09 (m, 4H, NH—$CH_2C$=O), 3.18 (t, 1H, H-3), 3.62 (m, 4H, —NH—$CH_2$—, —$CH_2$—$NH_2$), 3.68 (d, 2H, H-6a, H-6b), 3.85 (s, 2H, —NH—$CH_2$—), 4.68 (t, 1H, H-1), 7.95 (m, 2H, NH), 8.32 (m, 2H, NH).

Preparation Example 8

Synthesis of Derivative (Compound-2f of Formula (2), G=1-β-D-Glucopyranosyl Group, n=16, $Z_1$=ED, Y=ylG, m=3, $Z_2$=Single Bond, and R=t-Butoxycarbonyl Group)

The derivative (Compound-2f) among the derivatives represented by General Formula (2) wherein G was a 1-β-D-glucopyranosyl group, n was 16, $Z_1$ was ED, Y was ylG, m was 3, $Z_2$ was a single bond, and R was a t-butoxycarbonyl group was synthesized according to the synthesis method of Compound-2a using t-butoxycarbonyl glycyl glycine succinimidyl ester. Compound-2f was confirmed through $^1$H-NMR$^1$.

$^1$H-NMR (DMSO-$d_6$ with a drop of $D_2O$, 60° C., 400 MHz) 4.69 (t, 1H, H-1), 3.75 (d, 2H, $NCH_2C$=O), 3.67 (s, 2H, $NCH_2C$=O), 3.65 (d, 2H, $NCH_2C$=O), 3.63 (m, 1H, H-6), 3.40 (m, 1H, H-6), 3.16 (m, 1H, H-4), 3.08 (m, 4H, $NCH_2CH_2N$), 3.05 (m, 3H, H-2, H-3, H-5), 2.04 (m, 4H, $CH_2C$=O), 1.47 (m, 4H, $CH_2$), 1.38 (s, 9H, $CH_3$), 1.24 (m, 24H, $CH_2$)

Example 1

Preparation of Organic Nanotube Having Inner Surface Hydrophobized by Binary Self-Assembly of Asymmetric Bipolar Lipid Molecule (Compound-1a) and Derivative (Compound-2a)

Figure 5:
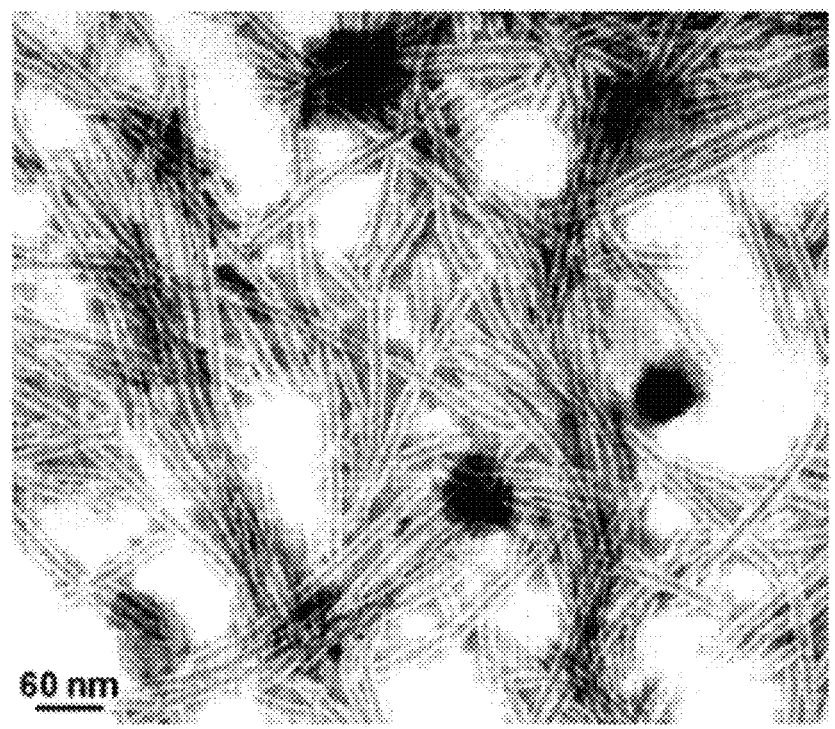
FIG. 5 is a photograph showing a transmission electron microscope image of an organic nanotube having a hydrophobized inner surface formed by self-assembly of two components (mixing ratio, Compound-1a of Formula (1): Compound-2a of Formula (2)=10:1) system of an asymmetric bipolar lipid molecule (Compound-1a of Formula (1), G=1-glucopyranosyl group, n=16, $Z_1$=ED, Y=ylG, m=3, and X=H) and a derivative thereof (Compound-2a of Formula (2), G=1-glucopyranosyl group, n=16, $Z_1$=ED, Y=ylG, m=3, $Z_2$=single bond, and R=benzyloxy carbonyl group).

A hydrochloride salt of an asymmetric bipolar lipid molecule (Compound-1a of Formula (1), wherein G=1-β-D-glucopyranosyl group, n=16, $Z_1$=ED, Y=ylG, m=3, and X=H, 7.3 μmol) and 0.6 mg of a derivative (Compound-2a, G=1-β-D-glucopyranosyl group, n=16, $Z_1$=ED, Y=ylG, m=3, $Z_2$=single bond, R=benzyloxy group, 5 mg, 0.73 μmol) were heated and dissolved in 5 ml of water (pH 5), and then the mixture was cooled to room temperature. Sodium hydroxide was added to the aqueous solution in which Compound-1a and Compound-2a were uniformly mixed to adjust the pH to 9 at room temperature. After negative staining using phosphotungstic acid, transmission electron microscope observation revealed a nanotube structure having an inner diameter of about 10 nm and a membrane thickness of about 3 nm (FIG. 5).

Example 2

Preparation of Organic Nanotube Having Inner Surface Hydrophobized by Binary Self-Assembly of Asymmetric Bipolar Lipid Molecule (Compound-1c) and Derivative (Compound-2e)

Figure 6:
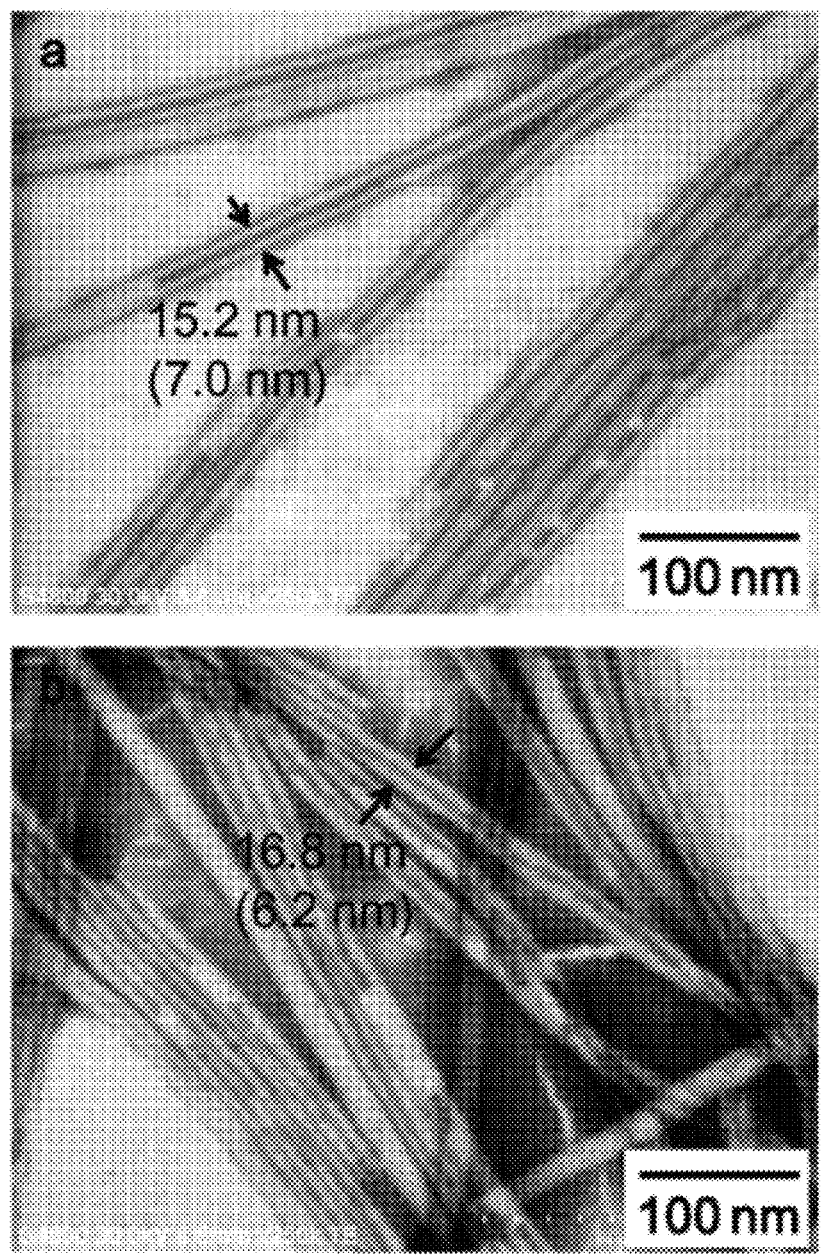
FIG. 6 is photographs showing transmission electron microscope images of an organic nanotube having a hydrophobized inner surface formed by binary self-assembly of an asymmetric bipolar lipid molecule (Compound-1c of Formula (1), G=1-glucopyranosyl group, n=18, $Z_1$=single bond, Y=Gly, m=4, and X=OH) and a derivative thereof (Compound-2e of Formula (2), G=1-glucopyranosyl group, n=18, $Z_1$=single bond, Y=Gly, m=3, $Z_2$=ED, and R=benzyloxy carbonyl group).

After an asymmetric bipolar lipid molecule 1c (Compound-1c of Formula (1), wherein G=1-β-D-glucopyranosyl group, n=18, $Z_1$=single bond, Y=Gly, m=4, and X=OH) and a derivative 2e (Compound-2e of Formula (2), wherein G=1-β-D-glucopyranosyl group, n=18, $Z_1$=single bond, Y=Gly, m=3, $Z_2$=ED, and R=benzyloxycarbonyl group) were mixed at a predetermined ratio (about 10:1 to 10:10) in DMSO, the mixture was heated and dissolved at 70° C., followed by cooling to room temperature, thereby performing binary self-assembly. Water (9-fold volume of DMSO) was added thereto to isolate the nanotube by filtering (200 nm), and then water was added (5 mg/ml), thereby obtaining an almost transparent nanotube dispersion solution. The derivative 2e alone gave Aan acicular crystal was as precipitated in the case of using the derivative 2e alone, but the mixture as described above formed almost transparent dispersion solution with excellent dispersibility. Further, as a result of observing this dispersion solution using an electron microscope, only nanotubular structures having an inner diameter of about 7 nm were obtained (FIG. 6). Therefore, it was found that the nanotube in a uniform molecular dispersion state was obtained by the binary self-assembly.

Example 3

Formation of Asymmetric Nanotube by Self-Assembly of Asymmetric Bipolar Lipid Molecule (Compound-1c of Formula (1), G=1-β-D-Glucopyranosyl Group, n=18, $Z_1$=Single Bond, Y=Gly, m=4, and X=OH)

First, in the following dissolving method by heating a dispersion solution and cooling method, using the asymmetric bipolar lipid molecule, Compound-1c, prepared in Preparation Example 5, the case of using water and dimethylsulfoxide as a solvent, respectively, will be described below.

In the case of preparation in water, the asymmetric bipolar lipid molecule (0.5 to 5 mg) was dispersed in 1 mL of pure water (milli Q water, or the like) and heated at 80 to 100° C. so as to be dissolved, followed by cooling (at 0.1 to 10° C./min), thereby obtaining an asymmetric nanotube. A shape and a size of the obtained asymmetric nanotube, or the like can be confirmed by dropping the dispersion solution onto a grid for an electron microscope and staining the inside with an electron beam impermeable stain. As described above, an asymmetric nanotube having an outer diameter of about 15 nm, an inner diameter of about 7 to 9 nm, and a length of 200 to 300 nm can be obtained (upper image of FIG. 7).

Similarly, the asymmetric bipolar lipid molecule (0.5 to 50 mg) was dispersed in 1 mL of dimethylsulfoxide and heated at 80 to 120° C. so as to be dissolved, followed by cooling (at 0.1 to 10° C./min), thereby obtaining a nanotube. A long nanotube having a tube length of about 5 to 10 μm can be obtained.

Similarly, in the case of using Compound-1d (in Formula (1), wherein G=1-β-D-glucopyranosyl group, n=18, $Z_1$=single bond, Y=Gly, m=6, and X=OH), an asymmetric nanotube having the same size can be obtained by the same process as described above (lower image of FIG. 7).

Example 4

Formation of Asymmetric Nanotube by Self-Assembly of Asymmetric Bipolar Lipid Molecule (Compound-2c of Formula (2), G=1-β-D-Glucopyranosyl Group, $Z_1$=Single Bond, Y=Gly, m=4, $Z_2$=Single Bond, and R=Methoxy Group)

A method of preparing an asymmetric nanotube using the asymmetric bipolar lipid molecule prepared in Preparation Example 4, that is, Compound-2c will be described.

The asymmetric bipolar lipid molecule (0.5 to 50 mg) was dispersed in 1 mL of dimethylsulfoxide and heated at 80 to 120° C. so as to be dissolved, followed by cooling (at 0.1 to 10° C./min), thereby obtaining an asymmetric nanotube having an outer diameter of about 15 nm and an inner diameter of about 7 to 9 nm (FIG. 8).

Example 5

Stability Evaluation of Tube Structure Under Physiological Conditions

FIG. 9 shows results of evaluating stability of various asymmetric nanotube structures under physiological conditions (after dispersing the nanotube in a PBS buffer (pH 7.4) and incubating for 32 hours). For comparison, two kinds of asymmetric nanotubes ("prior application nanotube A (corresponding to the case in which G was substituted with 2-glucopyrasylamine, n was 12, $Z_1$ was a single bond, Y was Gly, and m was 4 in General Formula 1)", "prior application nanotube B (corresponding to the case in which G was substituted with 2-glucopyrasylamine, n was 14, $Z_1$ was a single bond, Y was Gly, and m was 4 in General Formula 1)" in pending (Japanese Patent Application No. 2010-194544) as the related art and an asymmetric nanotube "conventional nanotube C (corresponding to the case in which G was substituted with 1-glucopyrasylamine, n was 16, $Z_1$ was a single bond, Y was Gly, and m was 2 in General Formula 1)" prepared by the method described in Non-Patent Literature 9 were used. These "prior application nanotubes A and B" and "conventional nanotube C" were mostly changed into a fibrous phase in all cases (FIGS. 9A to 9C). In this case, the structure was changed into a large tube structure having an inner diameter of about 50 nm and an outer diameter of about 100 to 150 nm.

Meanwhile, it was shown that the asymmetric nanotube obtained in Example 3 of the present invention did not show this change (FIG. 9D), and maintained the size of the formed nanotube in water, so that the asymmetric nanotube of the present invention had high structural stability under physiological conditions. In addition, although not shown, as a result of checking stability of the asymmetric nanotube obtained in Example 4 and the hydrophobized asymmetric nanotube obtained in Example 2 under the physiological conditions, there was no change in the shape. Therefore, it was found that these nanotubes had similar stability.

Example 6

Protein Refolding Function

Even when binary self-assembly of Compound-1a of Formula (1) and Compound-2a of Formula (2) was performed similarly in Example 1 in the presence of green fluorescent protein (GFP, 0.5 to 50 μg/μL) chemically denatured by guanidine hydrochloride (6 mol/L) or urea (8 mol/L), an organic nanotube having a hydrophobized inner surface having the same size dimension was formed. The organic nanotube having a hydrophobized inner surface was precipitated by centrifugation, thereby removing a supernatant containing GFP that was not encapsulated in the hollow cylinder. An operation of adding water thereto, performing centrifugation, and removing the supernatant was repeated several times. It was apparent that an amount of the denatured GFP encapsulated in the organic nanotube having a hydrophobized inner surface was about two times as much as that of denatured GFP capable of being encapsulated in an organic nanotube formed by single component self-assembly of the Compound-1a of Formula (1) (FIG. 10). The reason is that the organic nanotube having a hydrophobized inner surface interacted stronger with the denatured GFP having a structure in which the hydrophobic groups were partially exposed than the organic nanotube formed by single component self-assembly. It was found that in the case of decreasing a concentration of guanidine hydrochloride or urea to about 0.01 mol/L, the denatured GFP in the hollow cylinder of the organic nanotube was refolded. Refolding efficiency in the case of using the organic nanotube having a hydrophobized inner surface was significantly high as compared to the case of performing a general dilution method, and the refolding efficiency was about two times higher than that of the case of using an organic nanotube of which an inner surface was not hydrophobized (FIG. 11). The refolded normal GFP was anionic at near pH 7 and can be stably maintained in the hollow cylinder for a long period of time due to electrostatic interaction with amino groups on the inner surface of the protonated organic nanotube. Meanwhile, it was found that the electrostatic interaction was lost at near pH 8 by deprotonation of the amino group on the inner surface of the organic nanotube, so that normal GFP was released in bulk water (FIG. 12). It was found that a release rate of the normal GFP from the organic nanotube having a hydrophobized inner surface was faster than that of the organic nanotube of which the inner surface was not hydrophobized. It was apparent that only normal GFP was simply recovered by centrifugation.

Example 7

Protein Refolding Function 2

A hydrochloride salt of an asymmetric bipolar lipid molecule (Compound-1a of Formula (1), wherein G=1-β-D-glucopyranosyl group, n=16, $Z_1$=ED, Y=ylG, m=3, and X=H, 5 mg, 7.3 μmol) and a derivative (Compound-2f of Formula (2), wherein G=1-β-D-glucopyranosyl group, n=16, $Z_1$=ED, Y=ylG, m=3, $Z_2$=single bond, R=t-butoxycarbonyl group, 0.54 mg, 0.69 μmol) were heated and dissolved in 1 ml of water (pH 5), and then the mixture was cooled to room temperature. After adding carbonic anhydrase (CAB, 5 to 50 μg) chemically denatured by guanidine hydrochloride (6 mol/L) thereto, the pH was adjusted to 7 at room temperature using sodium hydroxide. After negative staining using phosphotungstic acid, it was confirmed through transmission electron microscope observation that a nanotube structure having an inner diameter of about 10 nm and a membrane thickness of about 3 nm was formed. The organic nanotube having a hydrophobized inner surface was precipitated by centrifugation, thereby removing a supernatant containing CAB that was not encapsulated in the hollow cylinder. An operation of adding water thereto, performing centrifugation, and removing the supernatant was repeated several times. It was found that an amount of the denatured CAB encapsulated in the organic nanotube having a hydrophobized inner surface was about two times as much as that of denatured CAB capable of being encapsulated in an organic nanotube formed by single component self-assembly of the Compound-1a of Formula (1) (FIG. 13). The reason is that the organic nanotube having a hydrophobized inner surface interacted stronger with the denatured CAB having a structure in which the hydrophobic groups were partially exposed than the organic nanotube formed by single component self-assembly. It was found that in the case of decreasing a concentration of guanidine hydrochloride or urea to about 1 mmol/L, the denatured CAB in the hollow cylinder of the organic nanotube was refolded. The CAB was released from the organic nanotube into bulk water under a condition of pH 7.8. A recovery rate of the refolded normal CAB was significantly high as compared to the case of simply diluting denatured CAB to refold (dilution method), and a recovery rate in the case of using the organic nanotube having a hydrophobized inner surface was 1.5 times higher than that in the case of using the organic nanotube of which the inner surface was not hydrophobized (FIG. 14).

Example 8

Function of Encapsulating Cationic Drug and Controlling Sustained-Release Property (Molar Ratio of Doxorubicin to Lipid in Nanotube: 1/8, and Amount of Doxorubicin: 239 μg/500 μL)

After an aqueous doxorubicin solution was added to 0.5 mL of dispersion solution (1.91 mg/mL, prepared at pH 6.5) of an organic nanotube of which an inner surface was hydrophobized by binary self-assembly of Compound-1c and Compound-2e obtained by the method in Example 2 in milli Q water, encapsulation capacity was investigated. As a result, this nanotube had encapsulation capacity almost equal to or slightly higher than that of the nanotube obtained from Compound-1c monolith (FIG. 15).

Then, release of the encapsulated doxorubicin from the nanotube was evaluated. That is, after sealing the nanotube encapsulating doxorubicin (molar ratio of doxorubicin to lipid in nanotube: 1/8, and amount of doxorubicin: 239 μg/500 μL) in a dialysis tube, an amount of doxorubicin released into an outer aqueous phase was quantified while stirring (200 rpm) using a spectrophotometer and 20 ml of HEPES-saline buffer (20 mM, HEPES; 150 mM NaCl, prepared at pH 7.4 or 5.5) as the outer aqueous phase. As a result, it was found that the release rate was significantly changed according to the ratio of the hydrophobic functional groups on the inner surface of the nanotube (FIG. 16). In addition, it was found that when the pH of the dispersion solvent was decreased from 7.4 to 5.5, the release rate was increased (comparison of FIGS. 16 and 17). Since it is known that cancer tissue changes to a slightly acidic state, this release property can become a superior property of promoting selective release of a drug in cancer tissue.

Example 9

Drug Encapsulation Experiment

An experiment of encapsulating doxorubicin was performed using the asymmetric nanotube prepared from Compound-1c in Example 3 and the "prior application nanotube A" as follows.

Two hundred micro litter of doxorubicin (dissolved in 2, 1, 0.714, 0.625, 0.555, 0.5 mg/mL milli Q water, respectively) and 200 μL of the respective dispersion solution (5 mg/mL) of asymmetric nanotube were mixed with each other and left at room temperature for 30 minutes. Two hundred micro litter of the mixture was extracted, filtered through a porous membrane (200 nm), and then washed with 400 μL of milli Q water. The obtained solid was redispersed in 200 μL of milli Q water. UV absorption by doxorubicin of the solution before and after filtering at 480 nm were compared with each other, thereby obtaining an encapsulation ratio. FIG. 18A shows an encapsulation ratio in the case of the asymmetric nanotube (prior application nanotube A) in pending (Japanese Patent Application No. 2010-194544) as the related art, and FIG. 18B shows an encapsulation ratio in the case of the asymmetric nanotube prepared in Example 3 of the present invention.

As a result, in the case of the nanotube according to the present invention, when the molar ratio (ONT/DOX) of the nanotube/doxorubicin was 5/1 to 11/1, encapsulation ratio was 95% or more. Therefore, it was found that high encapsulation ratio can be achieved only by mixing the nanotube and doxorubicin (FIG. 18B). In addition, in the case of "the prior application nanotube A", encapsulation of doxorubicin by similarly mixing the nanotube and doxorubicin was confirmed, but when ONT/DOX was 5/1, the encapsulation ratio (75%) was lower than that in the case of the nanotube according to the present invention by 20% (FIG. 18A). Further, in order to achieve an encapsulation ratio of 95% or more, a tube in which ONT/DOX was 7/1 or more was essential. Therefore, it was found that the asymmetric nanotube according to the present invention had a high doxorubicin encapsulation ratio. In addition, it was confirmed through electron microscope observation that the shape of the nanotube after encapsulation was not changed.

Example 10

Drug Release Experiment

Next, experiments of releasing drug from the nanotube encapsulating doxorubicin according to the prior art as described above (in Example 9) and from two kinds of nanotubes obtained according to the present invention were performed by a dialysis method in a PBS buffer (pH 7.4 and 5.5). The results were shown in FIGS. 19A and 19B, respectively. As shown in FIG. 19B, it was found that in the case of the asymmetric nanotube according to the present invention, in the vicinity of neutral pH (pH 7.4), a release amount was 50% of the entire encapsulation amount after 12 to 13 hours, and even after 32 hours, the release amount was 70% of the entire amount, but in an acidic state (pH 5.5), the release amount was about 50% in about 5 hours, and the encapsulated doxorubicin was entirely released in 25 hours. Meanwhile, as shown in FIG. 19A, in the case of using "the prior application nanotube A", 50% of doxorubicin was released in about 4 hours at pH 7.4. That is, it was found that in the nanotube according to the present invention, the release rate was decreased to ⅓, so that excellent sustained-release property was obtained. The reason is assumed that as shown in FIG. 9, in the nanotube according to the present invention, the tube structure was maintained after 32 hours under physiological conditions, but "the prior application nanotube A" was changed into the fibrous morphology after the same time. In addition, as shown in FIG. 20, it was found that in the nanotube according to the present invention, the tube structure was maintained after the drug release experiment. As described above, it was suggested that stability of the tube shape of the nanotube under physiological conditions was extremely important for the sustained-release property of the drug.

It was suggested that under a weak acidic condition (pH 5.5), the nanotube according to the present invention also had a more excellent sustained-release property as compared to the prior art. Under the weak acidic condition, drug release was accelerated as compared to the neutral condition. This indicates that protonation of carboxylate generated in carboxyl groups covered on the inner surface of the asymmetric nanotube can stimulate and accelerate release of the anticancer agent. Since cancer tissue or cells are generally in an acidic state (low pH) as compared to normal cells, release of the anticancer agent was accelerated under a low pH condition, which makes it possible to expect selective drug release in cancer tissue, so that the nanotube can be significantly effectively used as a drug capsule.

Example 11

Evaluation of Cationic Drug In Vitro

Cytotoxicity Evaluation of Drug Composition In Vitro

Cytotoxicity of various asymmetric nanotubes encapsulating doxorubicin obtained in Example 8 was evaluated as follows. That is, HeLa cells ($1 \times 10^4$) and various nanotubes encapsulating doxorubicin obtained in Example 8 were added into a 96-well plate so that concentrations of doxorubicin became equal to each other, using a Dulbecco's modified eagle medium (DMEM) added with fetal bovine serum (10%) as a cell culture medium for encapsulation and cultured at 37° C. under 5% $CO_2$ atmosphere for 24 hours. The concentration of doxorubicin was 0.01 to 20 μg/mL. Further, a molar ratio (Compound 1/Dox) of the tube to doxorubicin in the used encapsulation body was 7. As a control experiment, the same experiment was performed on doxorubicin. After culture, the supernatant was removed, and the obtained cells was washed with a PBS buffer (pH 7.4). Thereafter, cell viability was investigated through WST-8 assay, thereby calculating the half maximal inhibitor concentration ($IC_{50}$). In addition, similarly, cytotoxicity of the asymmetric nanotube itself was investigated using the nanotube obtained from Compound-1e in Example 3 (Table 2).

TABLE 2

| Sample | Asymmetric nanotube | Dox | Dox@asymmetric nanotube | Dox@hydrophobized asymmetric nanotube (6:2) | Dox@hydrophobized asymmetric nanotube (6:5) |
|---|---|---|---|---|---|
| $IC_{50}$ | 497.6 | 0.91 ± 0.12 | 1.12 ± 0.19 | 4.78 ± 0.63 | 8.65 ± 0.55 |

Doxorubicin (Dox), encapsulated doxorubicin in asymmetric nanotube, the half maximal inhibitor concentration ($IC_{50}$, μg/mL) of asymmetric nanotube.

First, it was suggested that since $IC_{50}$ of the asymmetric nanotube itself was about 0.5 mg/mL, the asymmetric nanotube had significantly low cytotoxicity and was a relatively safe compound for a living body. In addition, it was found that toxicity of encapsulated doxorubicin in the asymmetric nanotube was reduced as compared to that of doxorubicin itself. Particularly, in the hydrophobized asymmetric nanotube having an excellent sustained-release property, $IC_{50}$ was increased about 9 to 10 times. Therefore, it was found that the hydrophobized asymmetric nanotube had a significant toxicity reduction effect. As described above, the asymmetric nanotubes, particularly, the hydrophobized asymmetric nanotube had excellent effect of suppressing side effects.

The invention claimed is:

1. An organic nanotube having a hydrophobized inner surface, the organic nanotube comprising:
   an asymmetric bipolar lipid molecule represented by the following General Formula (1); and
   a derivative thereof represented by the following General Formula (2), wherein it is formed by binary self-assembly;

[Chemical Formula 1]

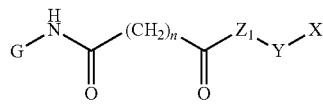

General Formula (1)

[Chemical Formula 2]

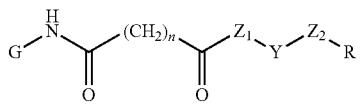

General Formula (2)

in Formulas (1) and (2), wherein the same symbols have the same meanings, and G is a 1-glucopyranosyl group or 2-glucopyranosyl group, n is an integer of 12 to 22, $Z_1$ and $Z_2$ are single bonds or

[Chemical Formula 3]

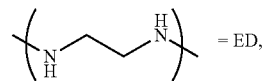

and when $Z_1$ is ED, $Z_2$ is a single bond

Y is

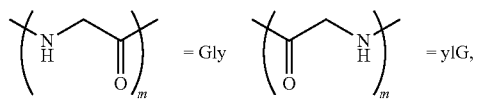

m is an integer of 2 to 6, and

X is OH when Y is Gly, and X is H when Y is ylG, and

R is a benzyloxycarbonyl group, a t-butoxycarbonyl group, a 9-fluorenylmethoxycarbonyl group, an acetyl group, an ethylcarbonyl group, a propylcarbonyl group, an alkoxy group having 1 to 4 carbon atoms, a benzyloxy group, or hydrophobic amino acid.

2. The organic nanotube of claim 1, wherein R is a methoxy group, an ethoxy group, or a t-butoxy group among alkoxy groups having 1 to 4 carbon atoms, or alanine, valine, leucine, isoleucine, methionine, proline, phenylalanine, or tryptophan among the hydrophobic amino acids.

3. The organic nanotube of claim 1, wherein in General Formulas (1) and (2), n is an integer of 18 to 22, both of $Z_1$ and $Z_2$ are single bonds, Y is Gly, m(s) are the same or different integer of 3 to 6, X is OH, and R is a methoxy, ethoxy, or benzyloxy group, and wherein the organic nanotube is a carboxylic acid based asymmetric nanotube formed from asymmetric bipolar lipid molecules represented by the following General Formulas (5) and (6);

[Chemical Formula 7]

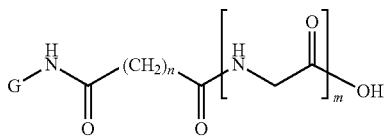

General Formula (5)

(wherein, n is an integer of 18 to 22, and m is an integer of 3 to 6,)

[Chemical Formula 8]

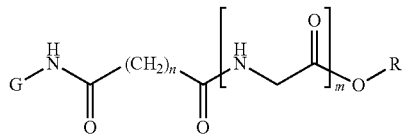

General Formula (6)

(wherein, n has the same meaning as that of General Formula (1), m indicates the same or different integer of 3 to 6, and R indicates a straight chain alkyl group having 1 to 4 carbon atoms).

4. A protein refolding agent comprising the organic nanotube having a hydrophobized inner surface of claim 1 as an active component.

5. A composition for releasing refolded normal protein formed by encapsulating the denatured protein in a hydrophobic hollow cylinder of the organic nanotube having a hydrophobized inner surface of claim 1.

6. A sustained-release encapsulation formulation of a hydrophobic drug comprising the organic nanotube having a hydrophobized inner surface of claim 1 as an active component.

7. An encapsulated hydrophobic drug composition formed by encapsulating a hydrophobic drug in a hydrophobic hollow cylinder of the organic nanotube having a hydrophobized inner surface of claim 1.

8. An asymmetric bipolar lipid molecule, a salt thereof, or an ester thereof represented by the following General Formulas (5) and (6);

[Chemical Formula 7]

General Formula (5)

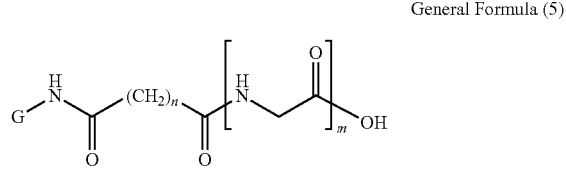

(wherein, n is an integer of 18 to 22, and m is an integer of 3 to 6),

[Chemical Formula 8]

General Formula (6)

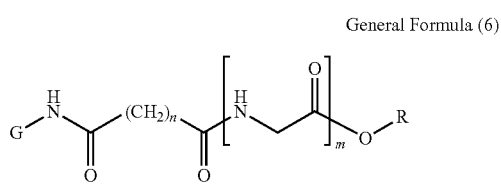

(wherein, n has the same meaning as that of General Formula (5), m indicates the same or different integer of 3 to 6, and R indicates a straight chain alkyl group having 1 to 4 carbon atoms).

9. A carboxylic acid based asymmetric nanotube formed by self-assembly of any one of the asymmetric bipolar lipid molecules of claim 8, salts thereof, and esters thereof, or a mixture thereof.

10. A sustained-release encapsulation formulation of a cationic drug comprising the carboxylic acid based asymmetric nanotube of claim 9 as an active component.

11. An encapsulated cationic drug composition, wherein the carboxylic acid based asymmetric nanotube of claim 9 encapsulates a cationic drug to form a cationic drug-asymmetric nanotube complex.

12. A cationic drug-asymmetric nanotube complex, wherein the carboxylic acid based asymmetric nanotube of claim 9 encapsulates a cationic drug.

13. A cationic drug composition comprising the cationic drug-asymmetric nanotube complex of claim 12 as an active component.

14. The cationic drug composition of claim 13, wherein the cationic drug is an anthracycline based anticancer agent having an amino group.

15. A method of preparing an organic nanotube having a hydrophobized inner surface of claim 1 comprising:
    mixing the asymmetric bipolar lipid molecules represented by General Formula (1) and the derivative represented by General Formula (2) in an aqueous solvent to perform binary self-assembly.

16. A method of refolding denatured protein comprising:
    encapsulating the denatured protein in the organic nanotube having a hydrophobized inner surface of claim 1 by dispersing the denatured protein and the organic nanotube in an aqueous solvent.

17. The method of refolding denatured protein of claim 16, further comprising:
    adding the denatured protein into an aqueous medium at the time of mixing an asymmetric bipolar lipid molecule and the derivative to perform the binary self-assembly.

18. A method of encapsulating a hydrophobic drug comprising:
    encapsulating the hydrophobic drug in an organic nanotube having a hydrophobized inner surface of claim 1 by dispersing the hydrophobic drug and the organic nanotube in an aqueous solvent.

19. The method of encapsulating a hydrophobic drug of claim 18, further comprising:
    adding the hydrophobic drug into an aqueous medium at the time of mixing the asymmetric bipolar lipid molecule and the derivative to perform the binary self-assembly.

20. A method of preparing a carboxylic acid based asymmetric nanotube comprising:
    dispersing a asymmetric bipolar lipid molecule or an ester thereof represented by General Formula (5) or (6) alone or dispersing a mixture thereof in dimethylsulfoxide, dimethylformamide, or water; and
    heating the resultant so as to be dissolved, and then cooling the resultant,

[Chemical Formula 7]

General Formula (5)

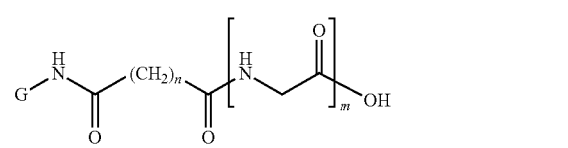

(wherein, n is an integer of 18 to 22, and m is an integer of 3 to 6),

[Chemical Formula 8]

General Formula (6)

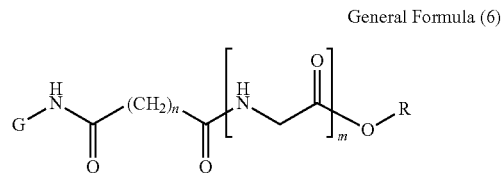

(wherein, n has the same meaning as that of General Formula (1), m indicates the same or different integer of 3 to 6, and R indicates a straight chain alkyl group having 1 to 4 carbon atoms).

* * * * *